US010940119B2

(12) United States Patent
Weissmueller et al.

(10) Patent No.: US 10,940,119 B2
(45) Date of Patent: Mar. 9, 2021

(54) NANO-ENCAPSULATION USING GRAS MATERIALS AND APPLICATIONS THEREOF

(71) Applicant: THE TRUSTEES OF PRINCETON UNIVERSITY, Princeton, NJ (US)

(72) Inventors: Nikolas T. Weissmueller, Princeton, NJ (US); Robert K. Prud'Homme, Lawrenceville, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 0 days.

(21) Appl. No.: 15/751,689

(22) PCT Filed: Aug. 8, 2016

(86) PCT No.: PCT/US2016/046052
§ 371 (c)(1),
(2) Date: Feb. 9, 2018

(87) PCT Pub. No.: WO2017/027474
PCT Pub. Date: Feb. 6, 2017

(65) Prior Publication Data

US 2018/0228736 A1 Aug. 16, 2018

Related U.S. Application Data

(60) Provisional application No. 62/203,167, filed on Aug. 10, 2015.

(51) Int. Cl.

| | |
|---|---|
| ***A61K 9/51*** | (2006.01) |
| ***B82Y 5/00*** | (2011.01) |
| ***C09D 189/00*** | (2006.01) |
| ***C08L 89/00*** | (2006.01) |

(52) U.S. Cl.
CPC .............. *A61K 9/5169* (2013.01); *B82Y 5/00* (2013.01); *C08L 89/00* (2013.01); *C09D 189/00* (2013.01)

(58) Field of Classification Search
CPC ......... B82Y 5/00; C08L 89/00; C09D 189/00; A61K 9/5169
See application file for complete search history.

(56) References Cited

U.S. PATENT DOCUMENTS

| | | | | |
|---|---|---|---|---|
| 8,137,699 B2 * | 3/2012 | Johnson | A01N 25/04 | 424/501 |
| 8,211,205 B1 * | 7/2012 | Didenko | B22F 9/24 | 75/371 |
| 2012/0195947 A1 * | 8/2012 | Perumal | A61K 31/07 | 424/401 |

FOREIGN PATENT DOCUMENTS

| | | |
|---|---|---|
| EP | 0 644 771 A1 * | 3/1995 |
| EP | 0 644 771 B1 | 8/2002 |

OTHER PUBLICATIONS

Regier et al. ("Fabrication and characterization of DNA-loaded zein nanospheres" in Journal of Nanobiotechnology, 2012, pp. 1-13).*
Zhang et al. ("Fabrication, characterization and antimicrobial activities of thymol-loaded zein nanoparticles stabilized by sodium caseinate-chitosan hydrochloride double layers" in Food Chemistry 142, 2014, pp. 269-275).*
International Search Report and Written Opinion, issued in corresponding International Application No. PCT/US2016/046052, dated Dec. 20, 2016.
Regier, MC et al., "Fabrication and characterization of DNA-loaded zein nanospheres", Journal of Nanobiotechnology, vol. 10, Dec. 2, 2012, title; abstract; figure 2C; pp. 3-5, 9.
Zhang, Y et al., "Fabrication, characterization and antimicrobial activities of thymol-loaded zein nanoparticles stabilized by sodium caseinate-chitosan hydrochloride double layers", Food Chemistry, vol. 142, pp. 269-275, Jul. 20, 2013, abstract; pp. 270 and 273.
Li, K-K et al., "Continuous preparation of zein colloidal particles by Flash NanoPrecipitation (FNP)", Journal of Food Engineering, vol. 127, pp. 103-110, Dec. 11, 2013; entire document.
Prud'Homme, B., "Flash NanoPrecipitation", Princeton, (retrieved from the internet: Mar. 10, 2016) <URL:http://research.princeton.edu/news/features/a/?id=6234> Dec. 9, 2011; entire document.
Fang, RH, "Large-Scale Synthesis of Lipid-Polymer Hybrid Nanoparticles Using a Multi-Inlet Vortex Reactor", Langmuir, vol. 28, pp. 13824-13829, Sep. 5, 2012; entire document.
Luo, Y. et al., "Zein-Based Micro-and Nano-Particles for Drug and Nutrient Delivery: A Review", Journal of Applied Polymer Science, (2014) DOI: 10.1002/APP.40696, pp. 1-12.

* cited by examiner

*Primary Examiner* — Blessing M Fubara
(74) *Attorney, Agent, or Firm* — J. Clinton Wimbish; Nexsen Pruet, PLLC

(57) ABSTRACT

In one aspect, methods of preparing composite nanoparticle compositions are described herein. For example, in some embodiments, a method comprises providing a zein solution stream, an organic fluid stream including at least one additive and at least one buffer fluid stream. The zein solution stream, organic fluid stream and buffer fluid stream are delivered to a chamber for mixing at one or more rates sufficient to flash precipitate composite nanoparticles including the additive encapsulated by a shell comprising the zein.

26 Claims, 28 Drawing Sheets

MIVM Formulation:

1) 100% EtOH 2mg/mL VitE(12mL/min)
2) 0.1M Sodium citrate pH7.5 (36mL/min)
3) 60% EtOH, 11mg/mL Zein + 0.13 mg/mL Pluronic F68 (12mg/mL)
4) 0.1M Sodium citrate pH7.5 (36mL/min)

Dialyzed then added to 0.01M HCl pH 2.0 and subjected to heat ramp from 25°C-60°C. Sizes and PDI remained stable.

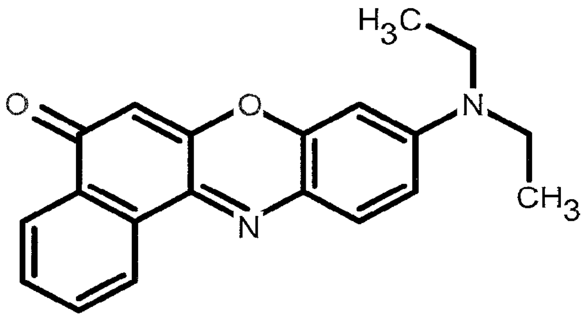
Nile Red (logP 3.65)
pH7.4 logD 4.46
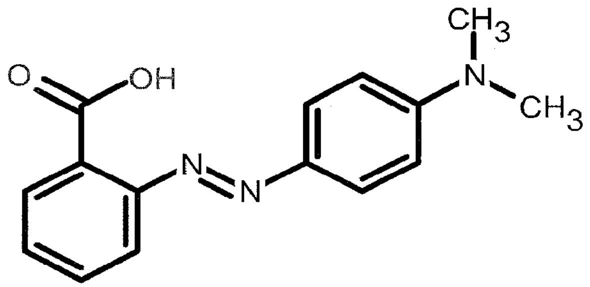
Methyl Red (logP 4.91)
pH7.4 logD 1.46
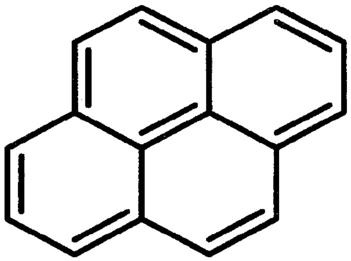
Pyrene (logP 5.17),
pH 7.4 logD 4.92
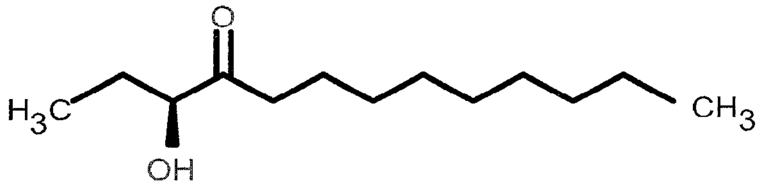
CAI-1 (logP 4.35)
pH 7.4 logD 4.30
FIGURE 5

FIGURE 10(a)

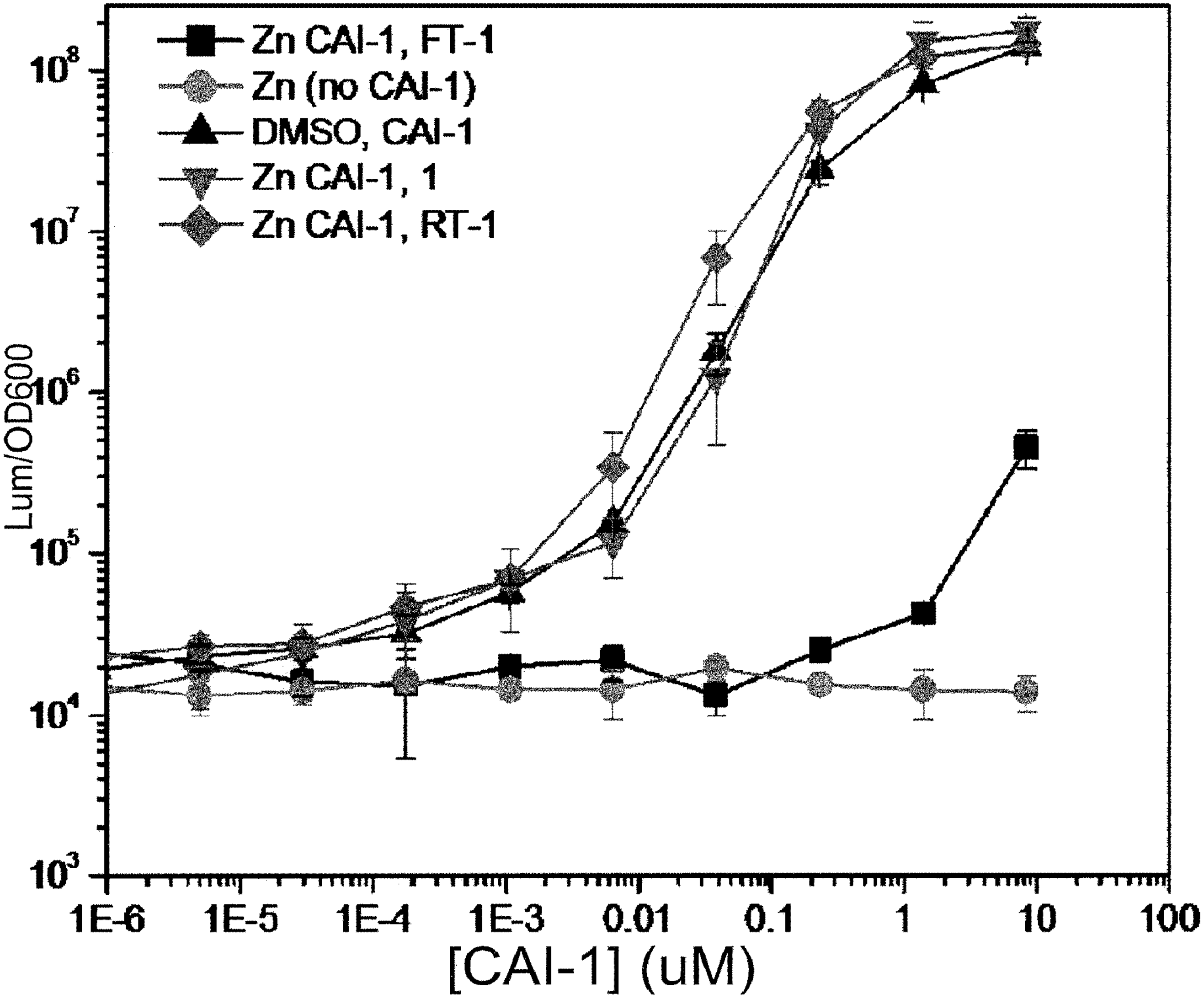

Figure 10: Quorum sensing activity of CAI-1 NCs. (A) Bioluminescence response of *vibrio cholerae* WNI102 supplemented with different amounts of CAI-1-loaded Zein:CAS:VitE-Ac NCs in PBS, CAI-1 in DMSO, CAI-1 in PBS, or zein NCs in PBS. Concentrated CAI-1 Zein:CAS:VitE-Ac NCs in PBS and CAI-1 in DMSO were added to cell cultures to the final concentrations indicated on the x-axis. CAI-1 in PBS, and Zein:CAS:VitE-Ac NCs in PBS were equivalently diluted and added to cell cultures.

FIGURE 10(b)

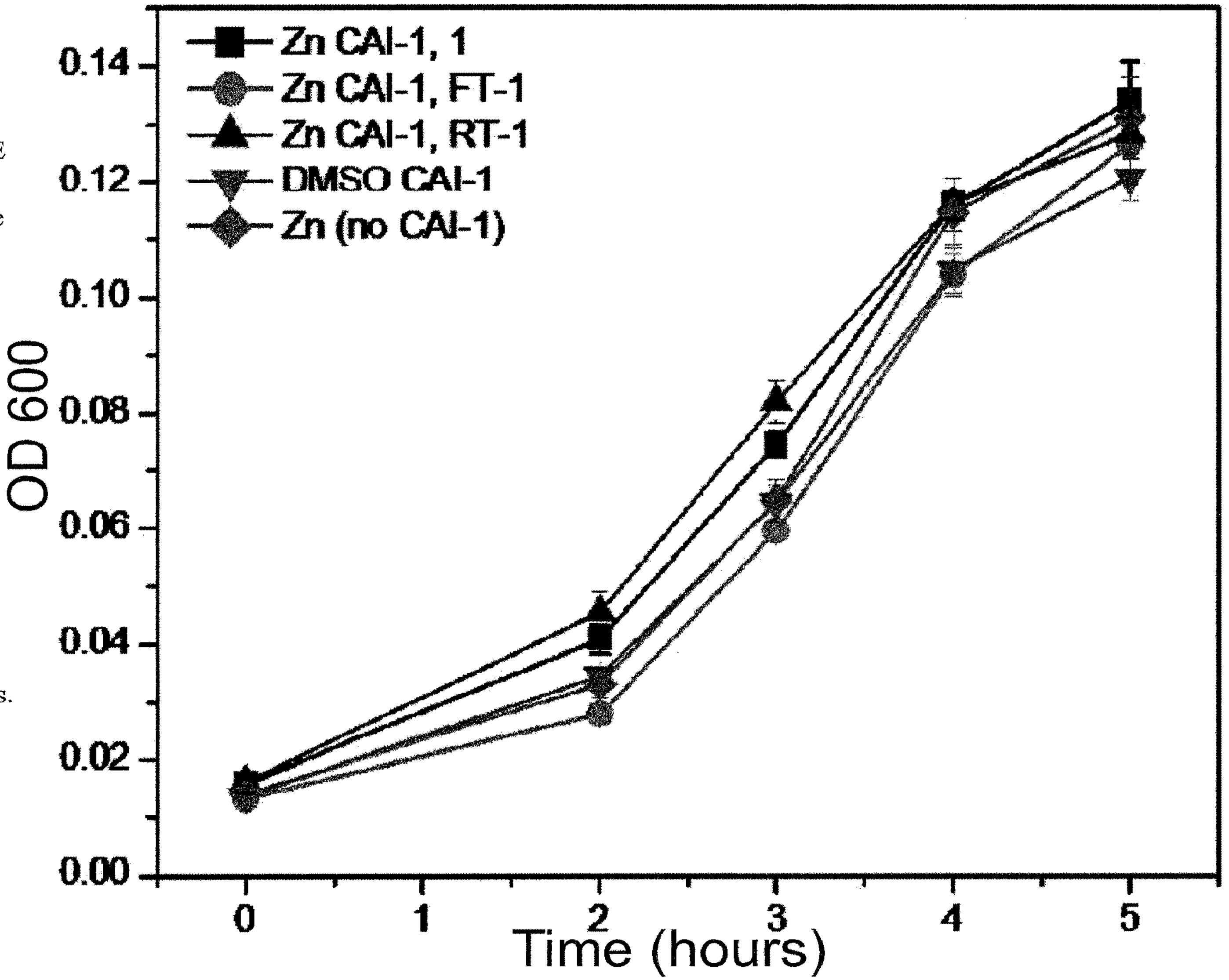

(B) Growth of *vibrio cholerae* cultures at 37°C. CAI-1 NCs do not alter *vibrio cholerae* cell growth. CAI-1 Zein:CAS:VitE-Ac NCs in PBS and CAI-1 in DMSO were added to cell cultures to final CAI-1 concentration of 50 μM. CAI-1 in PBS, and Zein:CAS:VitE-Ac NCs in PBS were equivalently diluted and added to cell cultures. In both panels, values are averages and error bars are standard deviations of three separate measurements.

| | Zein-F68 (1:120) | Zein-BSA-FITC (1:160) | Zein-DNA (1:200) | Zein/VitE Ac-Casein (12:1:9) |
|---|---|---|---|---|
| ■ Avg. Zeta Potential (mV) | -22 | -27 | -30 | -38 |

Formulations:

1) Mass ratio Zein:F68-Plutonic is 120:1
2) Mass ratio Zein:BSA-FITC is 120:1
3) Mass ratio Zein:DNA is 200:1
4) Mass ratio Zein:VitE-Ac:Casein is 12:1:9

| | Zein-F68 (1:120) | Zein-BSA-FITC (1:120) | Zein-DNA (1:200) | Zein/VitEAc-Casein (12:1:9) |
|---|---|---|---|---|
| **Avg. Zeta Potnetial (mV)** | **-21.9** | **-27.1** | **-29.6** | **-37.9** |
| **Std. Dev. (mV)** | **0.7** | **0.2** | **0.4** | **1.2** |

Zein Preformulations T=5min

| Description | Formulation | mQ | | PBS | | LB50 | |
|---|---|---|---|---|---|---|---|
| | | PDI | Z-Ave | PDI | Z-Ave | PDI | Z-Ace |
| Zn no core no surfactant | F1 | 0.013 | 128.0 | 0.192 | 538.9 | 0.184 | 561.6 |
| Zn no core 2wt% F68 | F2 | 0.020 | 125.8 | 0.179 | 556.8 | 0.140 | 605.7 |
| Zn no core 2wt% TPGS | F3 | 0.023 | 122.5 | 0.099 | 486.4 | 0.185 | 488.4 |
| Zn VitE-Ac no surfactant | F4 | 0.025 | 135.0 | 0.198 | 536.9 | 0.166 | 598.2 |
| Zn VitE-Ac 2wt% F68 | F5 | 0.031 | 185.5 | 0.053 | 264.8 | 0.151 | 617.3 |
| Zn VitE-Ac 2wt% TPGS | F6 | 0.052 | 146.7 | 0.161 | 562.9 | NA | NA |
| Zn 6mg/CAS 9mg no core | F7 | 0.131 | 84.56 | 0.132 | 88.41 | 0.107 | 93.53 |
| Zn 6mg/CAS 9mg 1mg VitE-Ac | F8 | 0.109 | 81.53 | 0.101 | 84.12 | 0.113 | 90.58 |
| Zn 6mg/CAS 9mg 5mg VitE-Ac | F9 | 0.087 | 97.73 | 0.079 | 100.6 | 0.068 | 106.5 |

FIG. 15

T=5hrs

| Description | Formulation | mQ | | PBS | | LB50 | |
|---|---|---|---|---|---|---|---|
| | | PDI | Z-Ave | PDI | Z-Ave | PDI | Z-Ace |
| Zn no core no surfactant | F1 | 0.033 | 225.1 | AG | AG | AG | AG |
| Zn no core 2wt% F68 | F2 | 0.046 | 220.9 | AG | AG | AG | AG |
| Zn no core 2wt% TPGS | F3 | 0.014 | 231.2 | AG | AG | AG | AG |
| Zn VitE-Ac no surfactant | F4 | 0.044 | 214.4 | AG | AG | AG | AG |
| Zn VitE-Ac 2wt% F68 | F5 | 0.210 | 287.7 | AG | AG | AG | AG |
| Zn VitE-Ac 2wt% TPGS | F6 | 0.029 | 188.9 | 0.61 | 4781 | 0.312 | 2137 |
| Zn 6mg/CAS 9mg no core | F7 | 0.154 | 88.93 | 0.116 | 89.54 | 0.13 | 94.42 |
| Zn 6mg/CAS 9mg 1mg VitE-Ac | F8 | 0.131 | 85.46 | 0.093 | 86.82 | 0.116 | 92.06 |
| Zn 6mg/CAS 9mg 5mg VitE-Ac | F9 | 0.106 | 102 | 0.102 | 101.6 | 0.096 | 108.4 |

FIG. 16

| | T=5min Zein:CAS ratios | | PBS Z-Ave | PBS PDI | pH2.0 Z-Ave | pH2.0 PDI | LB50 Z-Ave | LB50 PDI | Bile salts 2% Z-Ave | Bile salts 2% PDI |
|---|---|---|---|---|---|---|---|---|---|---|
| 6mg 1.5mg | 4--1 | | 136 | 0.029 | 674 | 0.029 | 149 | 0.033 | 178 | 0.089 |
| 6mg 3mg | 2--1 | | 100 | 0.052 | 569 | 0.234 | 111 | 0.052 | 139 | 0.111 |
| 6mg 6mg | 1--1 | | 87 | 0.071 | 745 | 0.257 | 92 | 0.083 | 120 | 0.100 |
| | 1--1.5 | | 84.12 | 0.101 | | | 90.58 | 0.113 | | |

| T=5 hrs Zein:CAS ratios | | PBS Z-Ave | PBS PDI | pH2.0 Z-Ave | pH2.0 PDI | LB50 Z-Ave | LB50 PDI | Bile salts 2% Z-Ave | Bile salts 2% PDI |
|---|---|---|---|---|---|---|---|---|---|
| 4--1 | | 144 | 0.033 | 912 | 0.348 | 156 | 0.045 | 348 | 0.111 |
| 2--1 | | 102 | 0.050 | 669 | 0.240 | 112 | 0.044 | 237 | 0.029 |
| 1--1 | | 85 | 0.082 | 1322 | 0.194 | 90 | 0.075 | 176 | 0.065 |
| 1--1.5 | | 86.82 | 0.093 | | | 92.06 | 0.116 | | |

| t=2 days Zein:CAS ratios | | PBS Z-Ave | PBS PDI | pH2.0 Z-Ave | pH2.0 PDI | LB50 Z-Ave | LB50 PDI | Bile salts 2% Z-Ave | Bile salts 2% PDI |
|---|---|---|---|---|---|---|---|---|---|
| 4--1 | | 198 | 0.038 | 1152 | 0.504 | Cont. | Cont. | 635 | 0.126 |
| 2--1 | | 128 | 0.029 | 1975 | 0.337 | Cont. | Cont. | 430 | 0.075 |
| 1--1 | | 90 | 0.113 | aggregated | aggregated | Cont. | Cont. | 255 | 0.052 |

FIG. 17

| | | Pre-FD | | Post-FD (Resuspended) | |
|---|---|---|---|---|---|
| Formulation | Condition | Diameter (nm) | PDI | Diameter (nm) | PDI |
| 0 | milliQ H2O | 206.1 | 0.028 | AGGR | |
| 1 | KH2PO4 | AGGR | AGGR | AGGR | |
| 2 | Sodium Citrate | 206.5 | 0.021 | AGGR | |
| 3 | Maltodex Sod. Citr | AGGR | AGGR | AGGR | |
| 4 | Maltodex KH2PO4 | AGGR | AGGR | AGGR | |
| 5 | Sucrose KH2PO4 | 213.7 | 0.045 | 477 | 0.326 |
| 6 | Trehalose KH2PO4 | 212.4 | 0.038 | 515 | 0.425 |
| 7 | F68 | 212.6 | 0.046 | AGGR | |
| 8 | Maltodextrin Sod. Citr+F68 | AGGR | AGGR | AGGR | |
| 9 | Maltodextrin KH2PO4+F68 | AGGR | AGGR | AGGR | |
| 10 | Sucrose KH2PO4+F68 | 218.5 | 0.053 | 294.9 | 0.122 |
| 11 | Trehalose KH2PO4+ F68 | 218.9 | 0.064 | 378.2 | 0.231 |

FIG. 18

| Symbol | Stream 1 (60% EtOH) | | Stream 2 (100% EtOH) | | | Stream 3 & 4 (Aqueous Buffer) | |
|---|---|---|---|---|---|---|---|
| | Zein | | CAI-1 | VitE-Ac | | CAS | |
| | Conc (mg/ml) | Q (ml/min) | Conc. (mg/ml) | Conc. (mg/ml) | Q (ml/min) | Conc. (mg/ml) | Q (ml/min) |
| -□- | 2 | 12 | 0 | 0.33 | 12 | 1 | 36 |
| -○- | 2 | 12 | 0.33 | 0.33 | 12 | 1 | 36 |
| -△- | 4 | 12 | 0.33 | 0.66 | 12 | 2 | 36 |
| -▽- | 6 | 12 | 0.33 | 0.99 | 12 | 3 | 36 |

FIG. 19

NANO-ENCAPSULATION USING GRAS MATERIALS AND APPLICATIONS THEREOF

RELATED APPLICATION DATA

This application is a U.S. National Phase of PCT/US2016/046052, filed Aug. 8, 2016, which claims priority under 35 U.S.C. § 119(e) to U.S. Provisional Patent Application Ser. No. 62/203,167 filed Aug. 10, 2015, each of which are incorporated herein by reference in their entireties.

FIELD

The present invention relates to compositions fabricated by flash nanoprecipitation (FNP) and, in particular, to nanoparticle compositions employing generally recognized as safe (GRAS) materials.

BACKGROUND

Modulating individual monomer structures in synthetic polymers enables the design of nanoparticles with specific encapsulation and release characteristics, but many synthetic polymers are still subject to FDA approval and their cost can add substantially to the price of therapy. Biodegradable protein polymers, such as albumin, casein, gelatin, and chitosan, among others, have been investigated as all-natural low-cost alternatives.

Zein is a prolamin protein found in endoplasmic reticulum-derived protein vesicles of maize seeds and generally finds application as film coating excipient of pharmaceuticals. Zein is water-insoluble owing to its high content (>50%) of non-polar amino acids such as leucine, proline, alanine, and phenylalanine. Globular zein consists of four fractions that vary in molecular weight, composition, structure and solubility. These include α-zein (MW, 19-24 kDa; 75-80% of total protein), β-zein (17-18 kDa, 10-15%), γ-zein (27 kDa, 5-10%), and δ-zein (10 kDa).

The zein subcomponents are arranged into a tertiary structure that comprises nine homologous repeating units oriented in an anti-parallel sense and stabilized by hydrogen bonds. The majority of the molecular surface area comprises the hydrophobic α-helixes in anti-parallel orientation, while the glutamine rich turns create a hydrophilic surface at their top and bottom. Together, this assembly bestows zein with amphiphilic characteristics. These properties are reported to drive self-assembly into a variety of mesostructres including ribbons, sheets, tori, pores, and micro- and nanospheres. These structures were achieved mainly by either solvent evaporation or anti-solvent precipitation. Zein colloidal particles are water-insoluble and overall hydrophobic, which has limited their application across industries. Driven by hydrophobic association they may aggregate or form precipitates.

A variety of techniques have been employed to produce particulate zein structures. Nanoparticles, for example, have been formed by emulsion-stripping processes, which are inherently expensive, difficult to scale from laboratory to industrial scale, and result in somewhat broad particle size distributions because the initial emulsification produces a broad drop size distribution. Spray drying has been used, but leads to particles outside the desired nanoparticle size range, and leads to aggregation. While supercritical processing has been demonstrated, larger sized particles are produced, and the cost of supercritical processing precludes its application in low-cost commercial production.

In view of these disadvantages, new fabrication processes are required enabling control and reproducibility of zein nanoparticle architectures on the industrial scale.

SUMMARY

In one aspect, methods of preparing composite nanoparticle compositions are described herein. For example, in some embodiments, a method comprises providing a zein solution stream, an organic fluid stream including at least one additive and at least one buffer fluid stream. The zein solution stream, organic fluid stream and buffer fluid stream are delivered to a chamber for mixing at one or more rates sufficient to flash precipitate composite nanoparticles including the additive incorporated into the composite nanoparticle structure. In some embodiments, the additive is encapsulated by or incorporated in a shell comprising the zein. The additive, in some embodiments, is hydrophobic. Moreover, the zein solution stream, organic fluid stream and buffer fluid stream can be delivered to the chamber by independent feed lines, in some embodiments. Further, the zein fluid stream and/or buffer fluid stream can also comprise one or more stabilizers. In such embodiments, the stabilizers can be incorporated into the composite nanoparticle structure. Generally, the composite nanoparticles can exhibit an average size of 10 nm to 500 nm with polydispersity less than 0.15 or less than 0.1.

Alternatively, a method of zein nanoparticle fabrication comprises providing a zein solution stream and at least one organic fluid stream, wherein the zein solution stream and organic fluid stream are delivered to a chamber for mixing at one or more rates sufficient to flash precipitate zein nanoparticles into the organic fluid stream. Importantly, the zein nanoparticles exhibit a hydrophilic interior and hydrophobic exterior. This is in contrast to the preceding method wherein hydrophobic moieties of the zein are oriented to the nanoparticle interior for interaction with the additive(s) encapsulated by the zein. Zein nanoparticles having a hydrophilic interior can also display an average size of 10 nm to 500 nm with polydispersity of less than 0.3.

In additional embodiments, a method of zein nanoparticle fabrication comprises providing a zein solution stream, at least one buffer fluid stream and at least one aqueous fluid stream. One or more additives are included in the buffer and/or aqueous fluid streams. The one or more additives can be hydrophilic in some embodiments. The zein solution stream, aqueous stream and buffer fluid stream are delivered to a chamber for mixing at one or more rates sufficient to flash precipitate composite nanoparticles including the additive incorporated into the composite nanoparticle structure. In some embodiments, the one or more additives are encapsulated by or incorporated in a shell comprising the zein. The zein fluid stream, aqueous stream and buffer fluid stream can be delivered to the chamber by independent feed lines. Further, the zein fluid stream and/or buffer fluid stream can also comprise one or more stabilizers. In some embodiments, the stabilizers can be incorporated into the composite nanoparticle structure. Generally, the composite nanoparticles formed according to this method can exhibit an average size of 10 nm to 500 nm with polydispersity less than 0.15 or less than 0.1.

In a further aspect, methods of treating bacterial infections are described herein. A method of treating a bacterial infection comprises administering to a patient in need thereof a therapeutically effective amount of a composition comprising nanoparticles having a core-shell architecture, the core including one or more anti-bacterial agents and the shell comprising zein. The core-shell nanoparticles, in some embodiments, can be prepared according to methods described herein wherein the anti-bacterial agent is the additive encapsulated by a shell comprising zein.

These and other embodiments are described in further detail in the detailed description which follows.

BRIEF DESCRIPTION OF THE DRAWINGS

FIG. 1(*b*) is a transmission electron microscopy (TEM) image of composite zein nanoparticles according to some embodiments described herein.

FIG. 3(*b*) illustrates size and PDI of composite nanoparticles with a lipid co-core relative to surfactant identity according to some embodiments described herein.

FIG. 3(*c*) illustrates the effect of VitE-Ac incorporation on composite nanoparticle size as a function of mass relative to protein content according to some embodiments described herein.

FIG. 3(*d*) illustrate the effect of sodium caseinate mass on composite nanoparticle size according to some embodiments described herein.

FIG. 6(*b*) illustrates mean composite nanoparticle diameter relative to dye encapsulation by weight according to some embodiments described herein.

FIGS. 6(*c*) and 6(*d*) illustrate fluorescence excitation and emission spectra respectively of composite nanoparticles encapsulating dye according to some embodiments described herein.

FIG. 9(*b*) illustrates individual contribution of composite nanoparticle formulation components and their effect on size and PDI of resulting colloids according to some embodiments described herein.

FIG. 10(*a*) illustrates bioluminescence response of *V. cholerae* WN1102 supplemented with varying amounts of CAI-1-loaded Zein/CAS/VitE-Ac composite nanoparticles in PBS according to some embodiments described herein.

FIG. 10(*b*) illustrates growth of *V. cholera* cultures at 37° C. in response to addition of CAI-1-loaded Zein/CAS/VitE-Ac nanoparticles according to some embodiments described herein.

FIG. 15 characterizes solution stability of composite nanoparticles of various construction.

FIG. 16 characterizes solution stability of composite nanoparticles of various construction.

FIG. 17 characterizes solution stability of zein/casein nanoparticles.

FIG. 18 characterizes several properties of composite nanoparticles of various construction and composition.

FIG. 19 provides compositions and flow rates for forming nanocarrier species of FIG. 9(*a*) according to methods described herein.

DETAILED DESCRIPTION

Figure 1A:
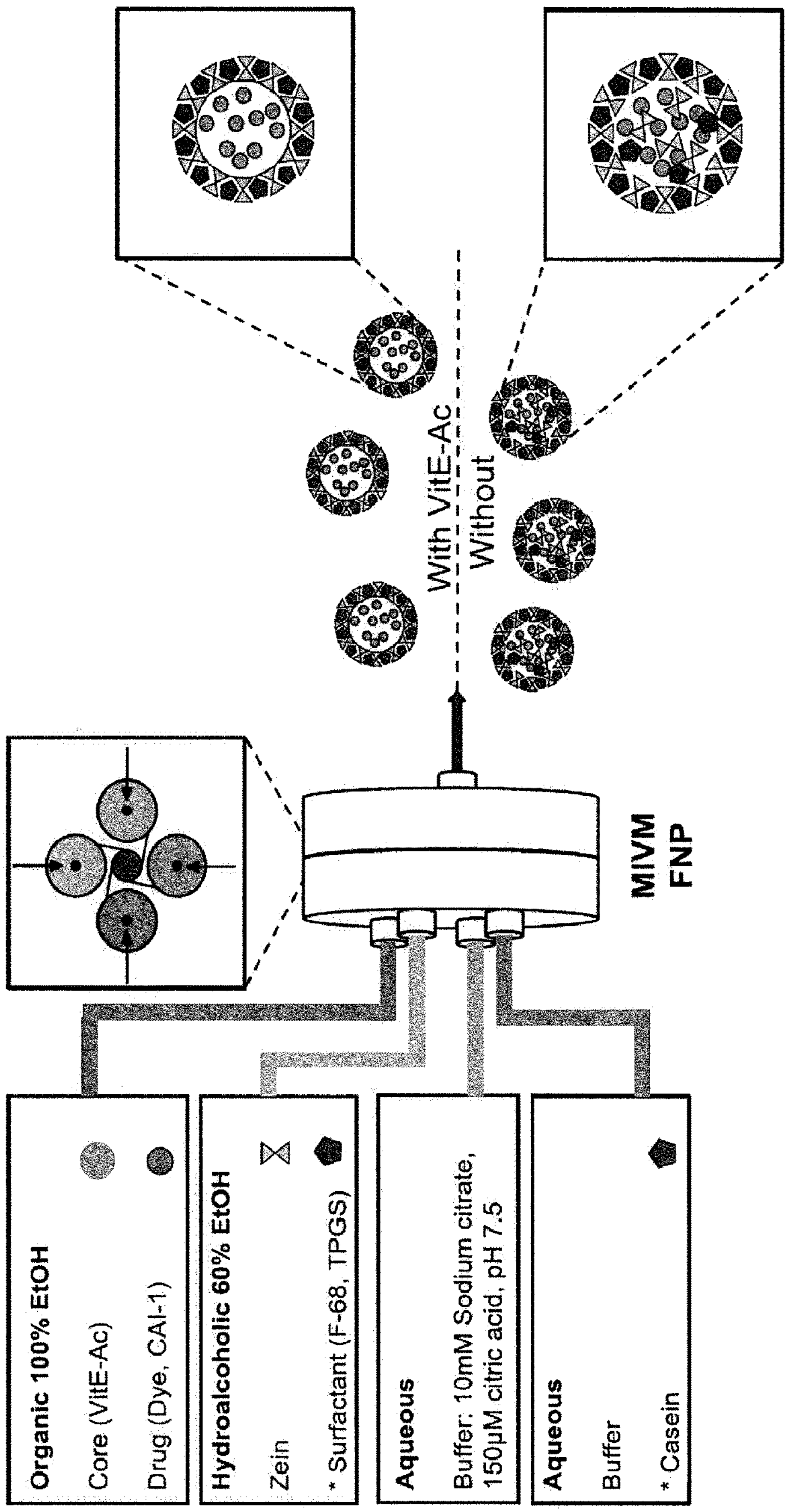
FIG. 1(*a*) is a schematic of a method and associated apparatus according to some embodiments described herein.

Embodiments described herein can be understood more readily by reference to the following detailed description and examples and their previous and following descriptions. Elements, apparatus and methods described herein, however, are not limited to the specific embodiments presented in the detailed description and examples. It should be recognized that these embodiments are merely illustrative of the principles of the present invention. Numerous modifications and adaptations will be readily apparent to those of skill in the art without departing from the spirit and scope of the invention.

I. Composite Nanoparticles

In one aspect, methods of preparing composite nanoparticle compositions are described herein. As the composite nanoparticle compositions can function as carriers for various additive species, the nanoparticle compositions can be considered nanocarriers. In some embodiments, a method comprises providing a zein solution stream, an organic fluid stream including at least one additive and at least one buffer fluid stream. The zein solution stream, organic fluid stream and buffer fluid stream are delivered to a chamber for mixing at one or more rates sufficient to flash precipitate composite nanoparticles including the additive incorporated into the composite nanoparticle structure. In some embodiments, the additive is encapsulated by a shell comprising the zein.

Turning now to specific steps, a zein solution stream is provided. As described in the examples herein, zein can be sourced from commercial sources. Alternatively, zein can be extracted from corn by a variety of methods such as those described in Shulka et al., Zein: the industrial protein from corn, *Industrial Crops and Products* 13 (2001) 171-192. Moreover, zein employed in the solution stream can also include zein derivatives. For example, zein can be modified to alter solubility and/or other properties without affecting formation of composite nanoparticles according to methods described herein. Any solvent not inconsistent with the objectives of the present invention can be used for the zein solution stream. In some embodiments, a hydroalcoholic solution serves as suitable solvent. Further, zein can be present in the solution in any amount not inconsistent with the objectives of the present invention. For example, zein can be present in an amount selected from Table I.

TABLE I

| Zein amount (mg/mL) |
|---|
| 1-10 |
| 2-9 |
| 4-8 |
| 5-10 |
| ≥10 |

In addition to the zein solution stream, an organic fluid stream is provided comprising at least one additive. Any organic fluid compatible with methods described herein can be employed. Organic fluid may vary depending on chemical identity of the one or more additives. In keeping with the GRAS characteristics of the present methods, suitable organic fluid can be ethanol. In other embodiments, hydrophobic solvents such as THF, DMSO, DMF or acetone may be employed. Further, a number of additives are contemplated, including hydrophobic additives and hydrophilic additives. Additive(s), for example, can be selected from pharmaceutical compositions, nutraceutical compositions, agricultural compositions, food and/or beverage compositions, taste-making compositions, biomolecular compositions and/or cosmetic compositions. In some embodiments, compositions include antibacterial agents, anti-parasitic agents, immunosuppressive agents, immunoactive agents, anticoagulants, antiviral agents, agro actives such as pesticides, fungicides, insecticides and fertilizers, diagnostic agents, imaging agents, dyes, anti-cancer agents, anti-oxidants, preservatives, vitamins, neutraceuticals and combinations thereof. Biomolecular compositions can include peptides, proteins, nucleic acids, nucleic acid fragments and combinations thereof. In some embodiments, nanoparticle compositions can be employed for taste-masking of undesirable taste of substances, such as bitter compounds. Non-limiting examples of agro additives, nutraceuticals and taste-masking agents contemplated for encapsulation can include:

| Agro Additive | Nutraceutical | Taste-masking Agent |
|---|---|---|
| Isofetamdid | Polyphenols (e.g. catechin, | Quinine |
| Azoxystrobin | kaempferol, quercetin, etc.) | Absinthin |
| Boscalid | Vitamins (e.g. Vit E, D, | Papaverine |
| Triademafon | K and derivatives s.a. | Cinnamedrine |
| Triticonazole | alpha tocopherol etc.) | Orphenadrin |
| Tebucanazole | Phospholipids | Haloperidol |
| Pyraclostrobin | Carotenoid | Yohimbine |
| Propriconazole | Fatty acid (e.g. Omega 3, | Adhumulone |
| Trifloxystrobin | a-linolenic acid (ALA), | Diphenidol |
| Penthiopyrad | EPA, DHA etc.) | Methadone |
| Carbosulfan | Phytostanol (e.g. | Isoxanthohumol |
| Etofenprox | campesterol, ergosterol, | Falcarindiol |
| Ethiprole | sitosterol, etc.) | Xanthohumol |
| Carbofuran | Curminoids | Consign |

-continued

| Agro Additive | Nutraceutical | Taste-masking Agent |
|---|---|---|
| Imidacloprid | (e.g. Curcumin, etc.) | Dicyclomine |
| 4-(2,4-dichlorophenoxy) butyrate DPBA | Ubiquinone, etc. | Colupulone |
| 2-(3-chlorophenoxy)propionate CPPA | | |
| Pendimethalin | | |
| Pheromones, s.a | | |
| Methyl eugenol | | |

As described herein, at least one buffer stream is also provided. Any suitable buffer composition not inconsistent with the objectives of the present invention can be employed. In some embodiments, pH of the buffer stream ranges from 7.0 to 8.0.

The zein solution stream, organic fluid stream and buffer stream are delivered to a chamber for mixing at one or more rates sufficient to flash precipitate composite nanoparticles comprising the additive(s) encapsulated by a shell comprising the zein. In some embodiments, the additive(s) are completely encapsulated by the shell comprising zein. In other embodiments, the additive(s) are partially encapsulated by the shell comprising zein. The zein solution stream, organic fluid stream and buffer fluid stream can be delivered to the mixing chamber at substantially the same rate. Alternatively, the solution streams can be delivered to the mixing chamber at differing rates. In some embodiments, for example, the solution streams are delivered to the mixing chamber according to Table II.

TABLE II

| Stream Delivery Rates | |
|---|---|
| Fluid Stream | Delivery Rate (mL/min) |
| Zein Solution | 10-20 |
| Organic | 10-20 |
| Buffer | 30-40 |

The mixing apparatus can employ independent feed lines and pumps for delivery of the individual fluid streams to the chamber. In some embodiments, the zein fluid stream, organic fluid stream and buffer fluid stream are simultaneously mixed in the chamber for flash precipitation of the nanoparticles. Alternatively, the fluid streams can enter the mixing chamber in any desired order resulting in composite nanoparticle production. Advantageously, methods described herein can permit continuous production of composite nanoparticles or batch production of composite nanoparticles. Suitable multi-inlet vortex mixing (MIVM) apparatus for methods described herein are described in U.S. Pat. No. 8,137,699 which is incorporated herein by reference in its entirety. In some embodiments, fluid stream enter the mixing chamber at velocities described in U.S. Pat. No. 8,137,699.

In some embodiments, the zein solution stream and the buffer fluid stream further comprise one or more stabilizers. Suitable stabilizers can include one or more surfactants, such as alkyl-oxide copolymers, polygycols and/or proteins, poloxamers and phospholipids, non-ionic surfactants, ionic surfactants, ionic- and nonionic lipids. Other surfactants that may be used in the method include other nonionic surfactants such as poloxamers (Pluronic), polyoxyethylene alkyl ethers (Brij), sorbitan esters (Span), polyoxyethylene sorbitan fatty acid esters (Tween), and ionic surfactants such as sodium dioctyl sulfosuccinate, sodium lauryl sulfate, benzalkonium chloride, cetyl trimethyl ammonium bromide, n-dodecyl trimethyl ammonium bromide, and polymer such as polyvinyl alcohol, polyvinyl pyrrolidone. Phospholipids that may be used in the method include non-ionic and charged lipids or phospholipids such as egg lecithin, soy lecithin, phosphatidyl choline, phosphatidyl ethanolamine, 1,2-dioleoyl-3-trimethyl ammonium propane. By way of example only, the surfactant or stabilizer may be Polysorbate 80, Polysorbate 60, copolymer condensates of ethylene oxide and propylene oxide, alpha-Hydro-omega-hydroxy-poly (oxyethylene)poly(oxypropylene), poly(oxyethylene) block copolymers, methyl glucoside, coconut oil ester, poloxalene, lecithin, hydroxypropylmethyl cellulose, casein, sodium caseinate, calcium caseinate, chitosan hydrochloride (CHC), tocopherol polyethylene glycol 1000 succinate, carboxymethyl cellulose, sorbitol, and glycerol. Examples of surfactants derived from natural plant oils are ethoxylated coca oils, coconut oils, soybean oils, castor oils, corn oils and palm oils. A surfactant and/or stabilizer can be or can be derived from a plant extract or a biodegradable plant extract. Many of these natural plant oils are U.S. FDA GRAS (Generally Recognized As Safe).

In some embodiments, for example, surfactant of the zein solution stream and/or buffer fluid stream is selected from tocopheryl polyethylene glycol succinate (TPGS), casein and ethylene oxide/propylene oxide surfactants under the PLURONIC® trade designation from BASF of Florham Park, N.J. Surfactant of the zein solution stream and/or buffer fluid stream can be incorporated into the composite nanoparticle structure. For example, surfactant can be incorporated into the hydrophobic core of the nanoparticle. Alternatively, surfactant can be incorporated into and/or onto the shell comprising zein. In further embodiments, surfactant can be incorporated into the core, shell and onto shell surfaces of the composite nanoparticles.

Figure 1B:
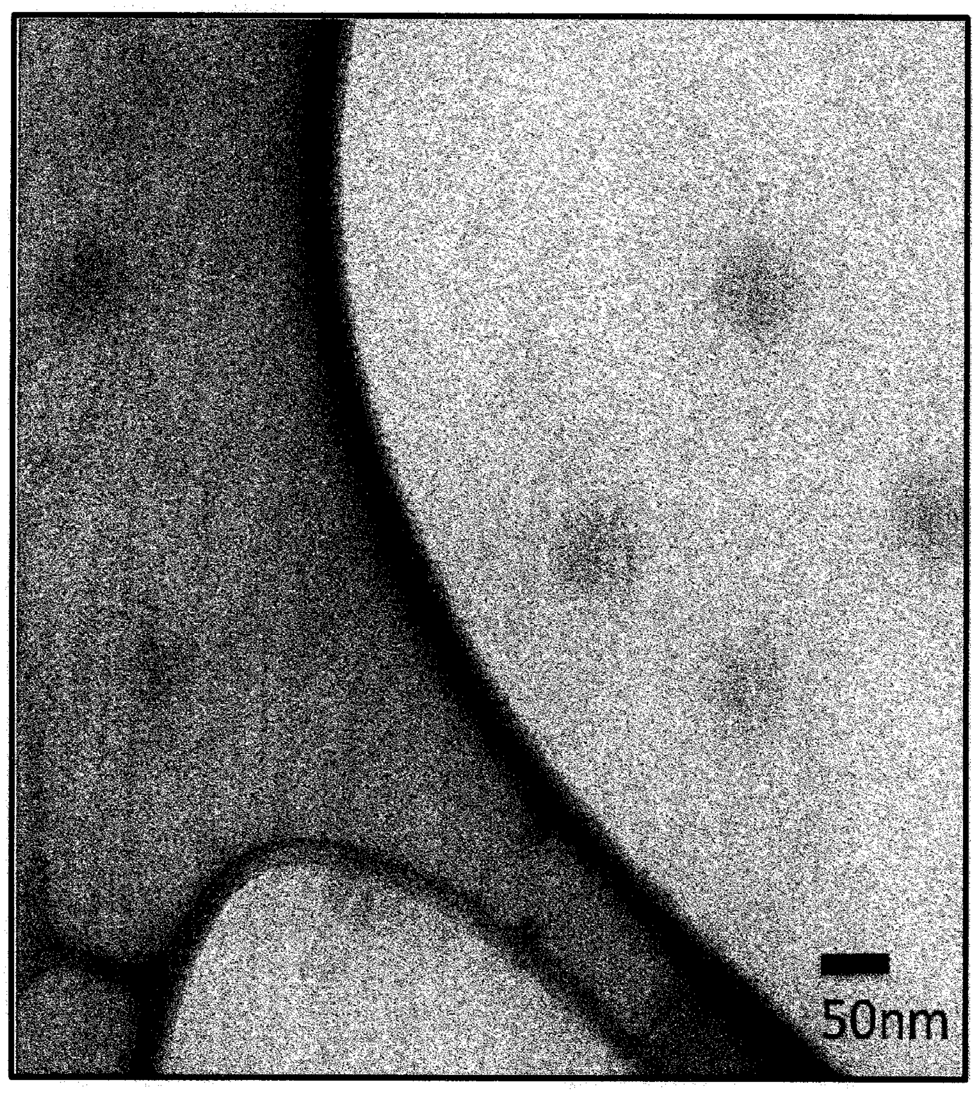

FIG. 1(*a*) is a schematic of a method and associated MIVM apparatus according to some embodiments described herein. As illustrated in FIG. 1(*a*), the zein solution stream, organic fluid stream and buffer fluid streams are delivered by independent lines to a vortex mixing chamber for the continuous production of composite nanoparticles. The zein solution stream and buffer stream contain surfactant that is incorporated into the core, shell and/or onto shell surfaces of the composite nanoparticles.

Alternatively, a method of zein nanoparticle fabrication comprises providing a zein solution stream, at least one buffer fluid stream and at least one aqueous fluid stream. One or more additives are included in the buffer and/or aqueous fluid streams. In some embodiments, for example, the additive(s) are hydrophilic including, but not limited to, hydrophilic additives listed in this Section I above. As set forth in the non-limiting examples herein, hydrophilic additive can include proteins, nucleic acids, nucleic acid fragments and/or combination thereof.

The zein solution stream, aqueous stream and buffer fluid stream are delivered to a chamber for mixing at one or more rates sufficient to flash precipitate composite nanoparticles including the additive(s) incorporated into the composite nanoparticle structure. In some embodiments, the one or more additives are fully or partially encapsulated by a shell comprising the zein. The zein fluid stream, aqueous stream and buffer fluid stream can be delivered to the chamber by independent feed lines. Further, the zein fluid stream and/or buffer fluid stream can also comprise one or more stabilizers. In some embodiments, the stabilizers can be incorporated into the composite nanoparticle structure. In some embodiments, the solution streams are delivered to the mixing chamber according to Table III.

TABLE III

| Stream Delivery Rates | |
|---|---|
| Fluid Stream | Delivery Rate (mL/min) |
| Zein Solution | 10-20 |
| Aqueous | 30-40 |
| Buffer | 10-40 |

Composite nanoparticles produced according to methods described herein having a hydrophobic or hydrophilic additive encapsulated by a shell comprising zein generally exhibit an average size of 10 nm to 500 nm. In some embodiments, the composite nanoparticles have an average size of 40 nm to 400 nm. Advantageously, the nanoparticles can have a polydispersity (PDI) of less than 0.15 or less than 0.1 in the as-formed state. Moreover, the nanoparticles can maintain a polydispersity of less than 0.15 or less than 0.1 in a variety of liquid carriers, including aqueous or aqueous-based liquid carriers. Fine control of nanoparticle size and polydispersity enables methods and associated nanoparticles described herein to find application in protein size standards. Additionally, the composite nanoparticles can comprise up to 60 wt. % of additive(s). In some embodiments, a composite nanoparticle has an additive loading selected from Table IV.

TABLE IV

| Composite Nanoparticle Additive Loading (wt. %) |
|---|
| 0.05-60 |
| 0.1-30 |
| 1-20 |
| 0.1-10 |
| 0.2-5 |
| 0.5-5 |

Moreover, methods described herein can generally exhibit additive encapsulation efficiency of 40-100 percent or 40-95 percent. In some embodiments, methods can exhibit additive encapsulation efficiency greater than 90%. In some embodiments, additive encapsulation efficiency is selected from Table V.

TABLE V

| Additive Encapsulation Efficiency (%) |
|---|
| ≥95 |
| ≥97 |
| ≥98 |
| 90-100 |

II. Zein Nanoparticles

In another aspect, methods of fabricating zein nanoparticles are described herein. For example, a method of zein nanoparticle fabrication comprises providing a zein solution stream and at least one organic fluid stream, wherein the zein solution stream and organic fluid stream are delivered to a chamber for mixing at one or more rates sufficient to flash precipitate zein nanoparticles into the organic fluid stream. Importantly, the zein nanoparticles exhibit a hydrophilic interior and hydrophobic exterior. This is in contrast to the preceding method of Section I wherein hydrophobic moieties of the zein are oriented to the nanoparticle interior for interaction with the hydrophobic additive(s) encapsulated by the zein. Zein nanoparticles having a hydrophilic interior can also display an average size of 10 nm to 500 nm with polydispersity of less than 0.3.

Turning now to specific steps, a zein solution stream is provided. The zein solution stream can be prepared in accordance with the disclosure in Section I above. Zein and/or zein derivatives, in some embodiments, are solubilized in a hydroalcoholic solution. Further, the amount of zein in the solution stream can be selected from Table I above. In some embodiments, zein may be modified to further enhance the hydrophilic character of the nanoparticle interior.

In addition to the zein solution stream, an organic fluid stream is provided. In keeping with the GRAS characteristics of the present methods, suitable organic fluid can be ethanol. In some embodiments, several organic fluid streams are provided. The zein solution stream and organic fluid stream(s) are delivered to a chamber for mixing at one or more rates sufficient to flash precipitate zein nanoparticles into the organic fluid stream. In some embodiments, for example, the solution streams are delivered to the mixing chamber according to Table VI.

TABLE VI

Stream Delivery Rates

| Fluid Stream | Delivery Rate (mL/min) |
|---|---|
| Zein Solution | 10-20 |
| Organic | 10-50 |

As in Section I, the mixing apparatus can employ independent feed lines and pumps for delivery of the individual fluid streams to the chamber. In some embodiments, the zein fluid stream and organic fluid stream are simultaneously mixed in the chamber for flash precipitation of the nanoparticles. Alternatively, the fluid streams can enter the mixing chamber in any desired order resulting in composite nanoparticle production. Advantageously, methods described herein can permit continuous production of composite nanoparticles or batch production of composite nanoparticles. Suitable MIVM apparatus are described in U.S. Pat. No. 8,137,699. In some embodiments, the apparatus illustrated in FIG. 1(*a*) can be employed wherein three of the feed lines are ethanol and the remaining feed line the zein solution.

III. Methods of Treating Infection

In a further aspect, methods of treating bacterial infections are described herein. A method of treating a bacterial infection comprises administering to a patient in need thereof a therapeutically effective amount of a composition comprising nanoparticles having a core-shell architecture, the core including one or more anti-bacterial agents and the shell comprising zein. The core-shell nanoparticles, in some embodiments, can be prepared according to methods described in Section I wherein the anti-bacterial agent is the hydrophobic additive encapsulated by a shell comprising zein. As detailed in the examples below, the anti-bacterial agent can be suitable for treating intestinal infections, such as cholera. Composite nanoparticle described herein, in some embodiments, demonstrate instability in bile salts, thereby enhancing drug delivery to environments containing such salts.

These and other embodiments are further illustrated by the following non-limiting examples.

Example 1—Fabrication and Characterization of Composite Nanoparticle Compositions Methods Materials Zein from maize (Z3625), casein sodium salt from bovine milk (C8654), Pluronic F-68 (P7061), α-Tocopheryl Acetate (VitE-AC) (T3001), Nile Red, (72485), Pyrene 98% (185515), and Citric acid (77929) were purchased from Sigma Aldirch (St. Louis, Mo.). Fisher BioReagents LB broth (BP9723) was used at 1× concentration. Sodium Citrate (F 0000-00-3) was purchased from Mallinckrodt. α-tocopheryl poly ethylene glycol 1000 succinate (TPGS 1000) was purchased from Eastman, and methyl red (M29610) from Fisher. CAI-1 was provided by the Semmelhack Research Group, Department of Chemistry, Princeton University. Reagents were of analytical grade. Ethanol (Fisher, BP 2818-4) was used as co-solvent for zein. NP preparation used milli-Q water, purified by reverse osmosis, ion-exchange and filtration.

Preparation of Surfactant Stabilized Zein Nanoparticles

Zein was suspended at 6 mg/mL in 60% EtOH. Surfactants TPGS or Pluronic F68, were added at 2% wt. relative to zein and the suspension sonnicated for 10 min. The zein-surfactant solution was rapidly mixed (12 mL/min) against an α-tocopheryl acetate (1 mg/mL in 100% EtOH, 12 mL/min) stream and a citrate buffer stream pH 7.5 (10 mM sodium citrate, 1.6 μM citric acid, 36 mL/min) using the MIVM mixer (FIG. 1), previously described. Flow rates were controlled by two Harvard Apparatus PHD2000 syringe pumps. The resulting solution contained 20% EtOH (v/v) and a zein/VitE ratio of 6:1 by mass.

Preparation of Casein Stabilized Zein Nanoparticles

Casein was dissolved at 1 mg/mL in citrate buffer pH 7.5 (10 mM sodium citrate, 1.6 μM citric acid) and sonnicated for 10 min. Zein was dissolved at 6 mg/mL in 60% EtOH and sonnicated. Casein (36 mL/min) and zein (12 mL/min) were rapidly mixed against an α-tocopheryl acetate (1 mg/mL in 100% EtOH, 12 mL/min) stream and a citrate buffer stream pH 7.5 (10 mM sodium citrate, 1.6 μM citric acid, 36 mL/min) within the MIVM geometry [FIG. 1(*a*)]. Dyes and CAI-1 were dissolved in the 100% EtOH solution containing 1 mg/mL α-tocopheryl acetate at various concentrations ranging from 0.1-10% wt relative to the particle core that comprised zein plus α-tocopheryl acetate. The resulting NP suspension contained 20% EtOH (v/v) with a relative mass of zein to casein to VitE of 6:3:1. To achieve different zein to casein ratios, the concentration of casein in citrate buffer was adjusted while respective flow rates of zein and casein solutions were kept the same.

Nanoparticle Characterization

Using a Zetasizer® Nano-ZS (Malvern instruments, Malvern, UK), dynamic light scattering (DLS) size measurements were performed on samples directly after FNP. Samples were diluted with ultra-pure water to avoid multiple scattering and analyzed at 25° C. using a detection angle of 173°. The reported size is the intensity-weighted average diameter as reported by the Malvern deconvolution software in Normal Mode analysis. Samples for TEM were prepared by placing 5 μL of the nanoparticle dispersion on an ultrathin carbon film on a holey carbon support film on 400 mesh copper grid (Ted Pella, Inc., Redding, Calif.) and drying under ambient conditions. The samples were imaged using a Philips CM100 TEM (Eindhoven, The Netherlands) operated at an accelerating voltage of 100 kV.

Fluorescence of Nile Red-loaded Zein NPs

The optical properties of Zn NPs were characterized with a F-7000 Fluorescence Spectrophotometer (Hitachi High Technologies America) after tenfold NP dilution in miliQ water. Emission scans were measured between a 530 nm to 800 nm window using a 500 nm excitation wavelength and 400 mV PMT voltage. Excitation scans were measured between a 400 nm to 670 nm window using a 690 nm emission wavelength at 400 mV PMT voltage.

Zein Nanoparticle Formulation

The encapsulation of poorly soluble actives into nanocarriers can enhance their bioavailability. Nanoparticle forming properties of zein using the FNP process (FIG. 1) were investigated. The herein presented FNP process using GRAS materials results in quasi monodisperse nanoparticles as evidenced by TEM [FIG. 1(*b*)]. The image depicts VitE-Ac containing zein/casein NPs (1.5:1 wt). Particles show a homogeneous size distribution of a darker core, comprising VitE and zein, and are surrounded by a faint halo of sodium caseinate as stabilizer [FIG. 1(*b*)].

Figure 2:
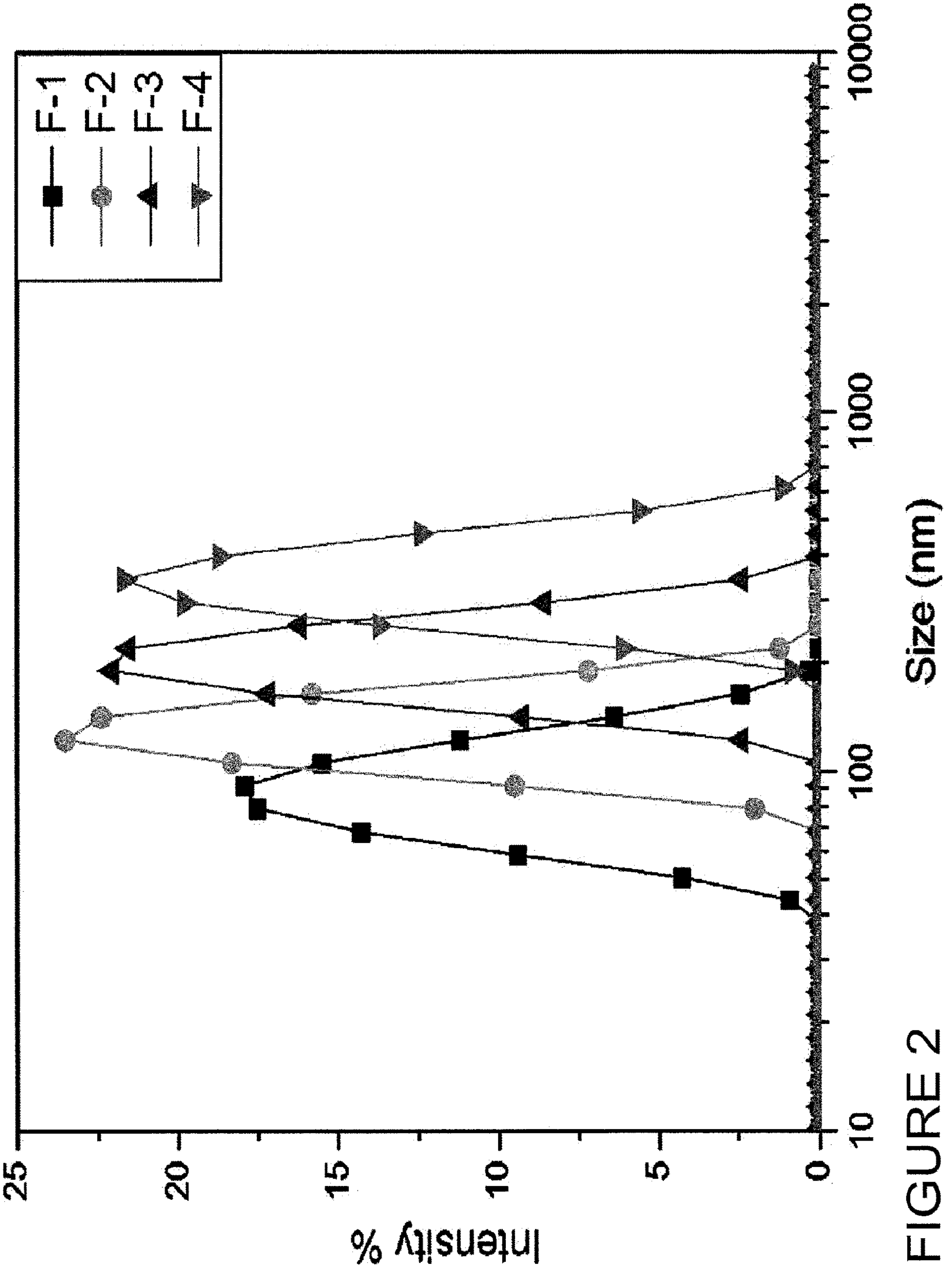
FIG. 2 illustrates nanoparticle size control according to some embodiments of methods described herein.

The encapsulation of a lipid co-core resulted in an increased mean particle diameter (from 127 nm to 199 nm) and PDI (from 0.008 to 0.026), while all other factors where held constant (FIG. 2*a*, formulations 'F-2' and 'F-3'). The addition of a basic amino acid, in this case lysine ('F−'), decreased the particle mean diameter (84 nm) but increased the PDI (0.076) despite the encapsulation of a lipid co-core. When an acidic moiety (malic acid) was incorporated in the formulation, the mean particle diameter (331 nm) increased. These results suggest that the mean nanoparticle diameter and PDI can be tuned by modulating the amount of the lipid co-core that is encapsulated, the addition of charged moieties, and an adjustment in solution pH (FIG. 2), while keeping all other variables constant.

Figure 3A:
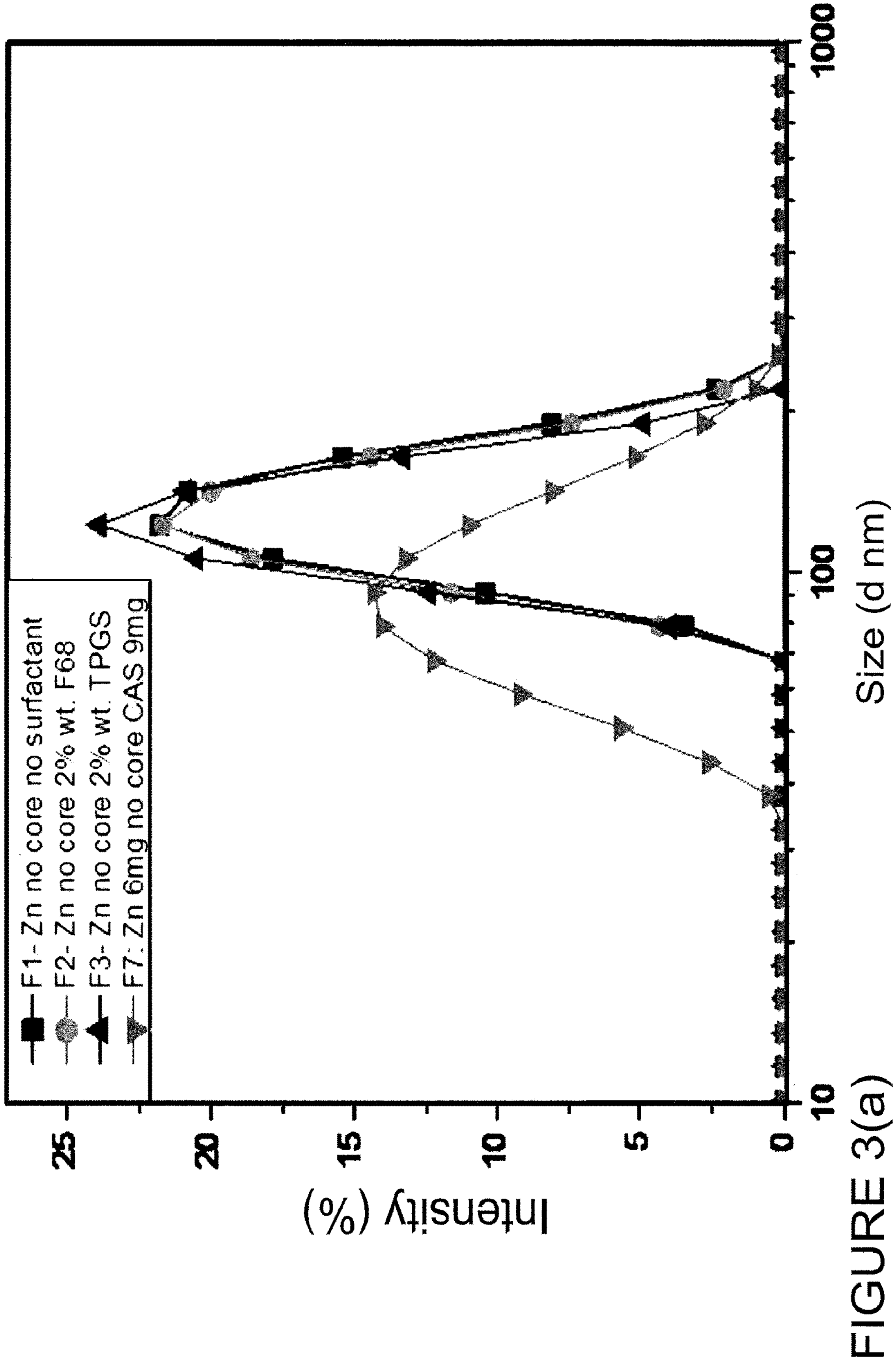
FIG. 3(*a*) illustrates size and PDI of zein nanoparticles without a lipid co-core relative to surfactant identity according to some embodiments described herein.
Figure 3B:
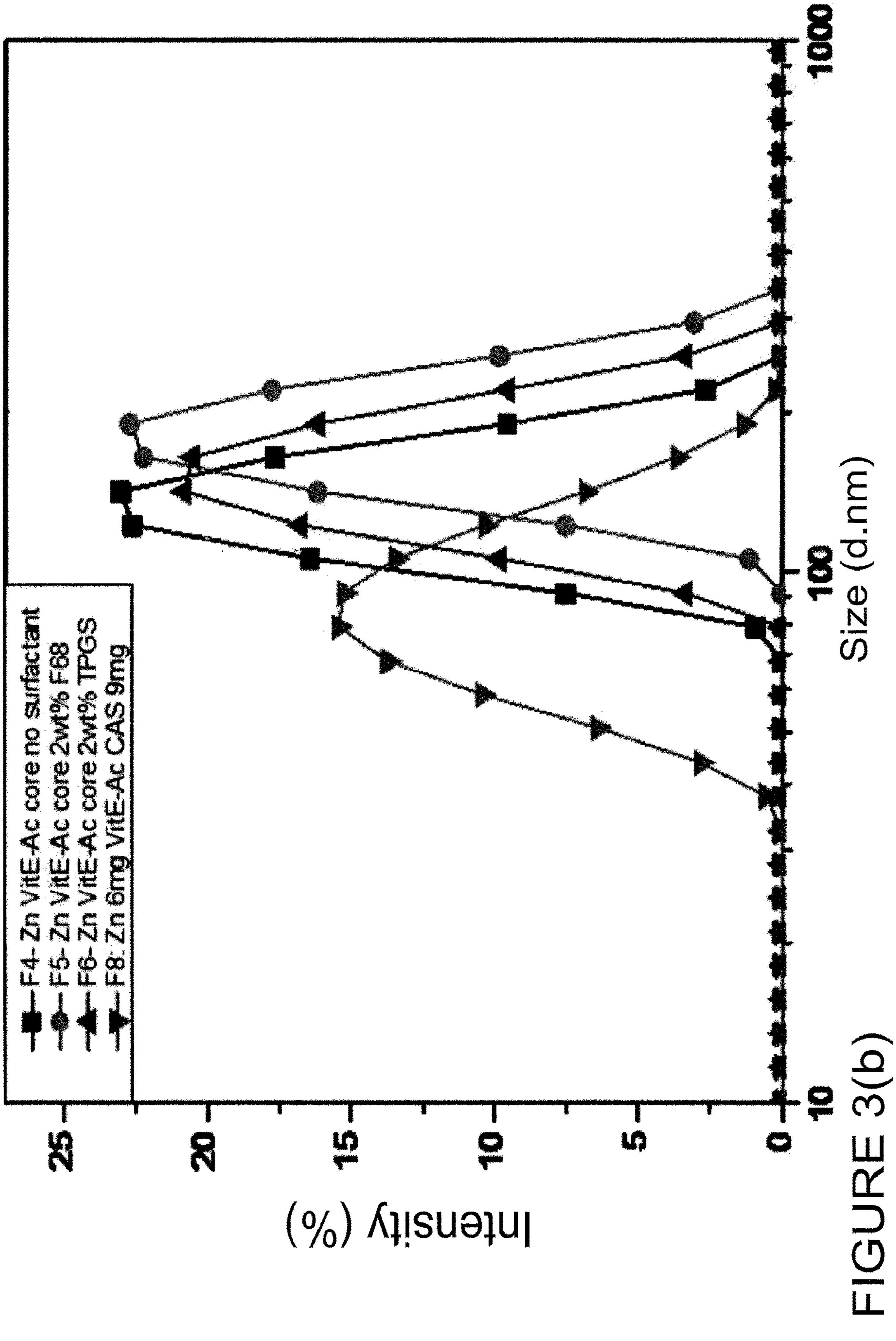
Figure 3C:
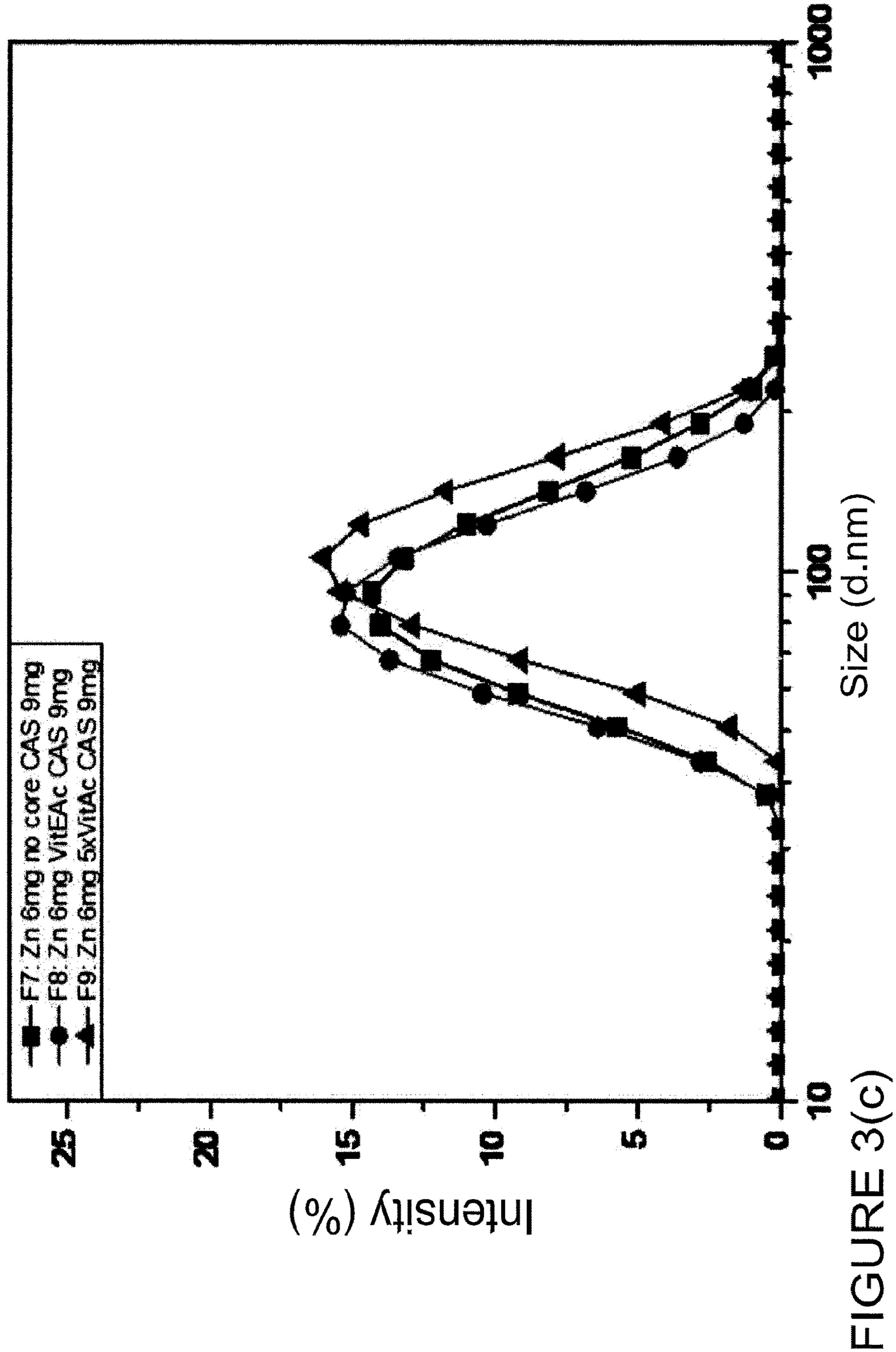
Figure 3D:
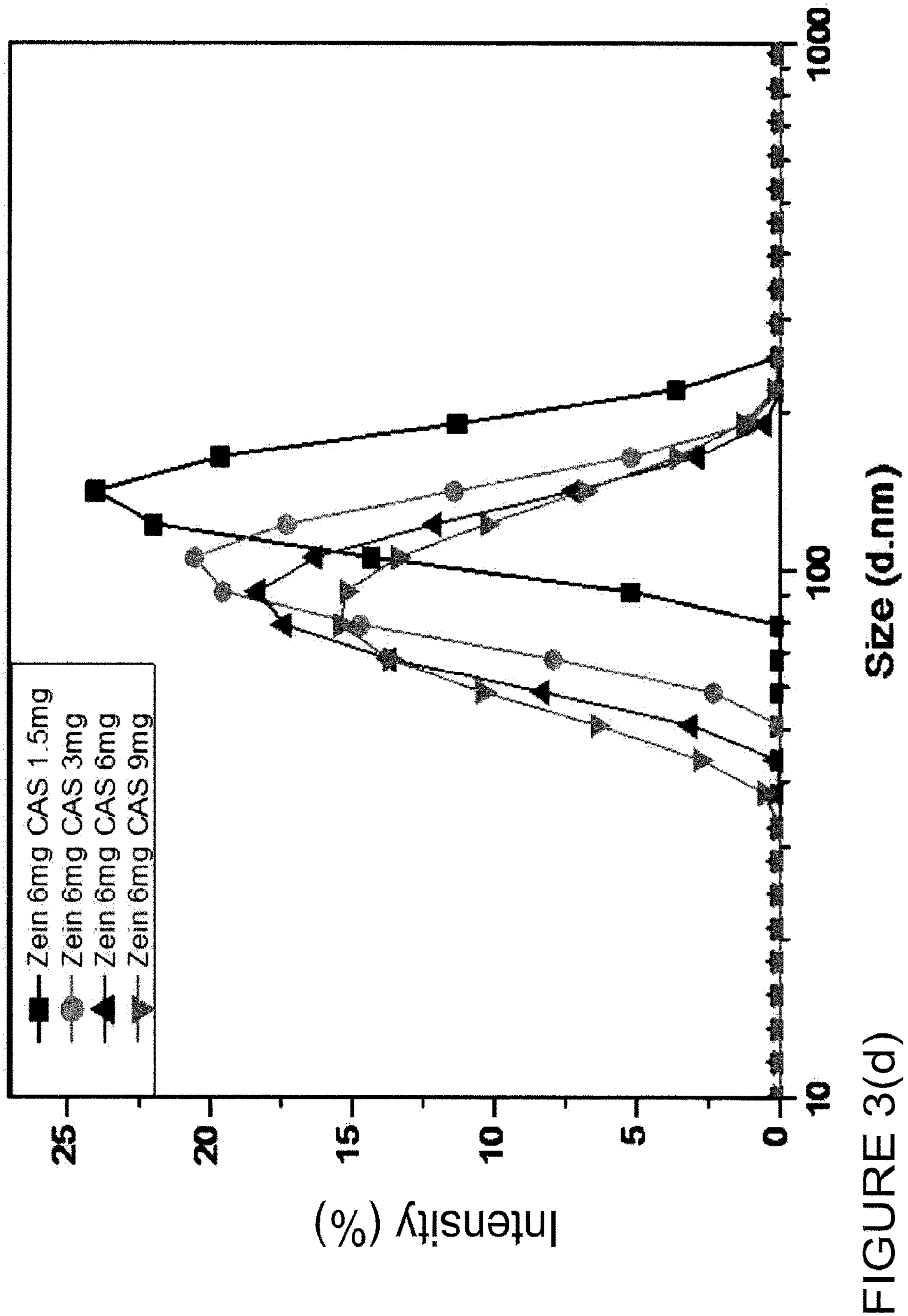

TPGS, Pluronic F68 and casein are FDA-approved surfactants. Their effect on particle characteristics and solution stability over time were examined by DLS. The size and PDI of zein NPs (ZNPs) was not affected by the addition of Pluronic F68 or TPGS, relative to unstabilized zein in milliQ water (FIG. 3*a*). When zein encapsulated a hydrophobic core comprising VitE-Ac (FIG. 3*b*), however, the mean diameter and PDI increased according to molecular weight of the surfactant relative to unstabilized ZNPs (ZNP<ZNP+TPGS<ZNP+F68). The use of casein as surfactant increased the PDI and reduced the mean ZNP diameter, regardless of whether VitE-Ac was encapsulated in the core or not. The encapsulation of VitE-Ac at a relative mass to zein of 1:6 shows little effect on the particle size and PDI, while at a ratio of 5:6 by weight, the resulting particles have a larger mean diameter (FIG. 3*c*). The increase of casein to zein ratio reduces mean particle size, while increasing the polydispersity (FIG. 3*d*). These results demonstrate good size control and reproducibility of the NP formation process.

Impact of Surfactants on Formulation Stability

Premature nanoparticle dissolution or aggregation would lead to delivery failure based on either too fast or too slow release of the active. Zein colloids aggregate in ionic solutions and during drying as result of hydrophobic interactions unless stabilized by surfactants. Initially, nanoparticle formulations were screened for stability at physiologic conditions (PBS) and conditions relevant to the in vitro model of *V. cholera*. While TPGS and Pluronic F68 were capable of stabilizing ZNPs in milliQ $H_2O$ (PDI≤0.052), these particles began aggregating within 5 minutes in PBS pH7.4 or LB50 (FIG. 15).

These formulations had completely aggregated within 5 hours. When ZNPs were stabilized by sodium caseinate, particles were stable in solution over 5 hours and even showed reduced polydispersity when loaded with ≤1 mg VitE-Ac ($PDI_{t=5min}$=0.109, $PDI_{t=5hrs}$=0.093). The stability behavior of ZNPs was independent of the VitE-Ac core (Tables VI, VII). The stabilization of hydrophobic colloids can be achieved by steric stabilization, electrostatic repulsion, or both. Close to the isoelectric point of zein (~pH6.8), steric stabilization with 2 wt. % TPGS or Pluronic F68 alone did not prevent aggregation. The isoelectric point of colloids containing sodium caseinate (~pH4.6) and zein has been reported to lie between the individual values and cause a surface charge reversal. The Zn/CAS stability at high ionic strength suggests an effective coverage of the zein and the importance of the electrostatic effect. Sodium caseinate sufficiently stabilized zein NPs manufactured by FNP in 1×PBS pH7.4 and LB50 broth.

Impact of Temperature on Nanoparticle Stability

Figure 4:
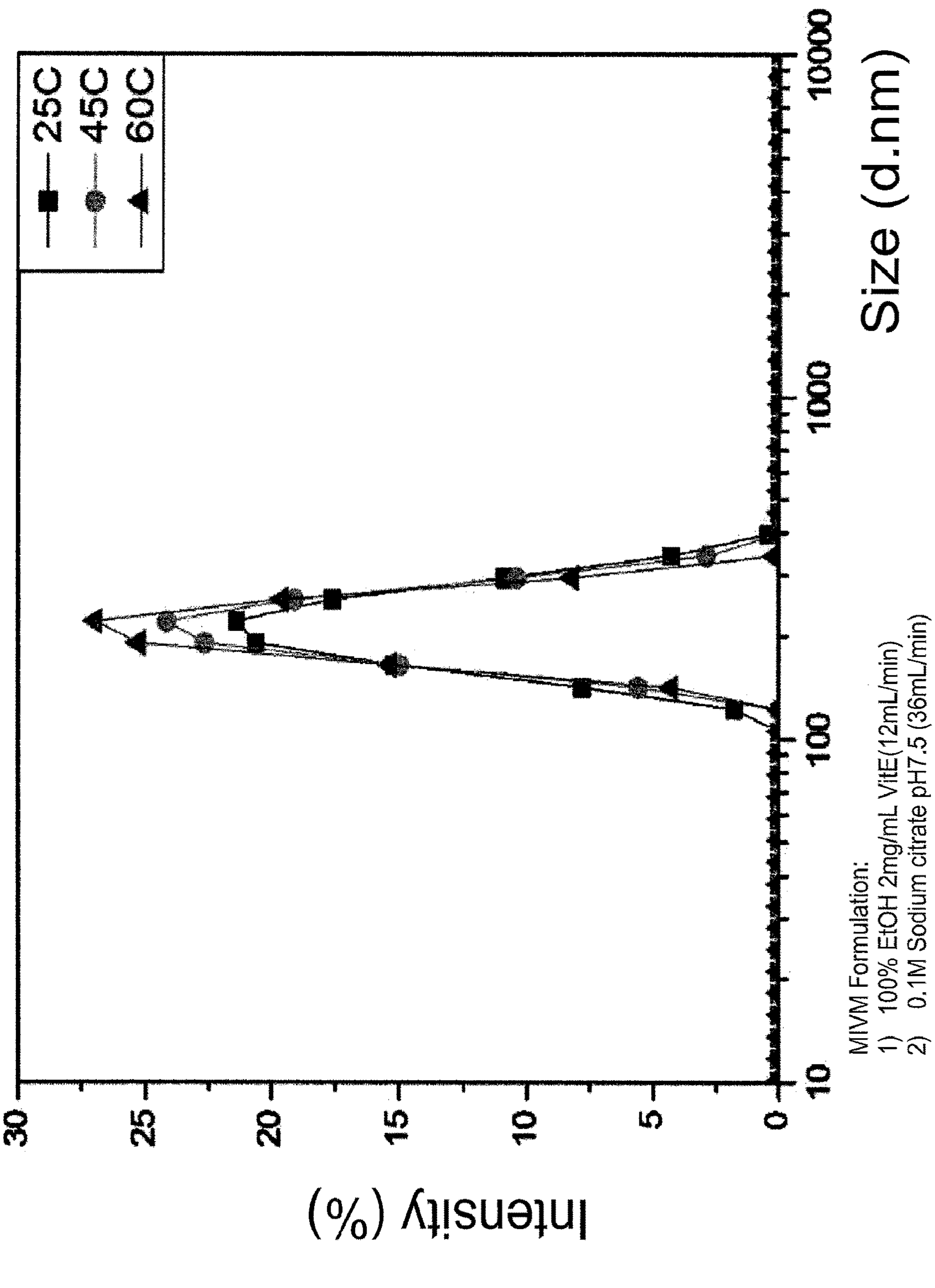
FIG. 4 illustrates composite nanoparticle size and PDI stability at various temperatures according to some embodiments described herein FIG. 5 illustrate molecular structures and characteristics of encapsulated dyes and autoinducer drug according to some embodiments described herein.

Increased temperature, as is the case in the human body, may also lead to premature nanoparticle dissolution or aggregation and would therefore lead to delivery failure based on either too fast or too slow release of the active. Zein particles containing a lipid co-core, and stabilized by PLURONIC F68, were stable during a 2 hour heat ramp from 25° C. to 60° C., suspended in 0.01M HCl pH 2.0 (FIG. 4). The specific diameters and PDI did not change significantly between temperatures 25° C. (206 nm, 0.045), 45° C. (210 nm, 0.005) and 60° C. (209 nm, 0.040).

Impact of Zn/CAS Ratio on Particle Characteristics and Stability

Various zein-to-casein ratios were produced to further investigate formulation stability in physiological environments relevant to oral delivery. Zein to casein ratios 4:1, 2:1, and 1:1 FIG. 17 in PBS, pH2.0, LB50 and 2% bile salts were investigated. In phosphate buffer, particles remained stable over 48 hrs with only minor changes in mean diameter or polydispersity. In the small intestine, bile salts emulsify and degrade lipids. While Zein/CAS/VitEAc NPs increased in size by about 40% when exposed to 2% bile salts, particles retained colloidal stability over 48 hrs FIG. 17. Specifically, Zein/CAS/VitEA NPs (2:1) showed best colloidal stability in PBS, 2% bile salts, LB50 and pH2.0 after 48 hrs FIG. 17.

Dye Encapsulation in Zein/CAS/VitEA Nanoparticles

Figure 6A:
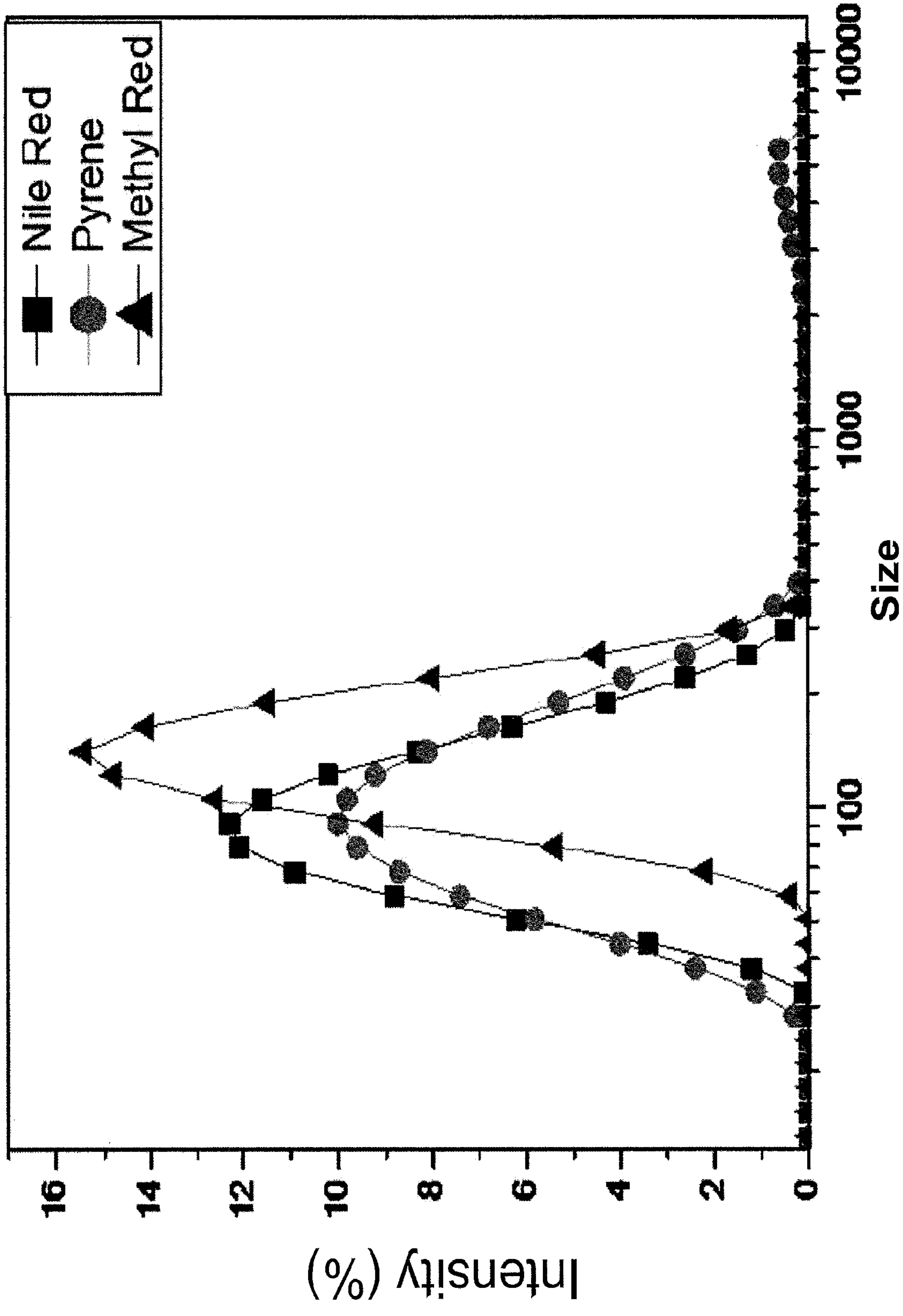
FIG. 6(*a*) illustrates composite nanoparticle size relative to the dye identity encapsulated according to some embodiments described herein.
Figure 6B:
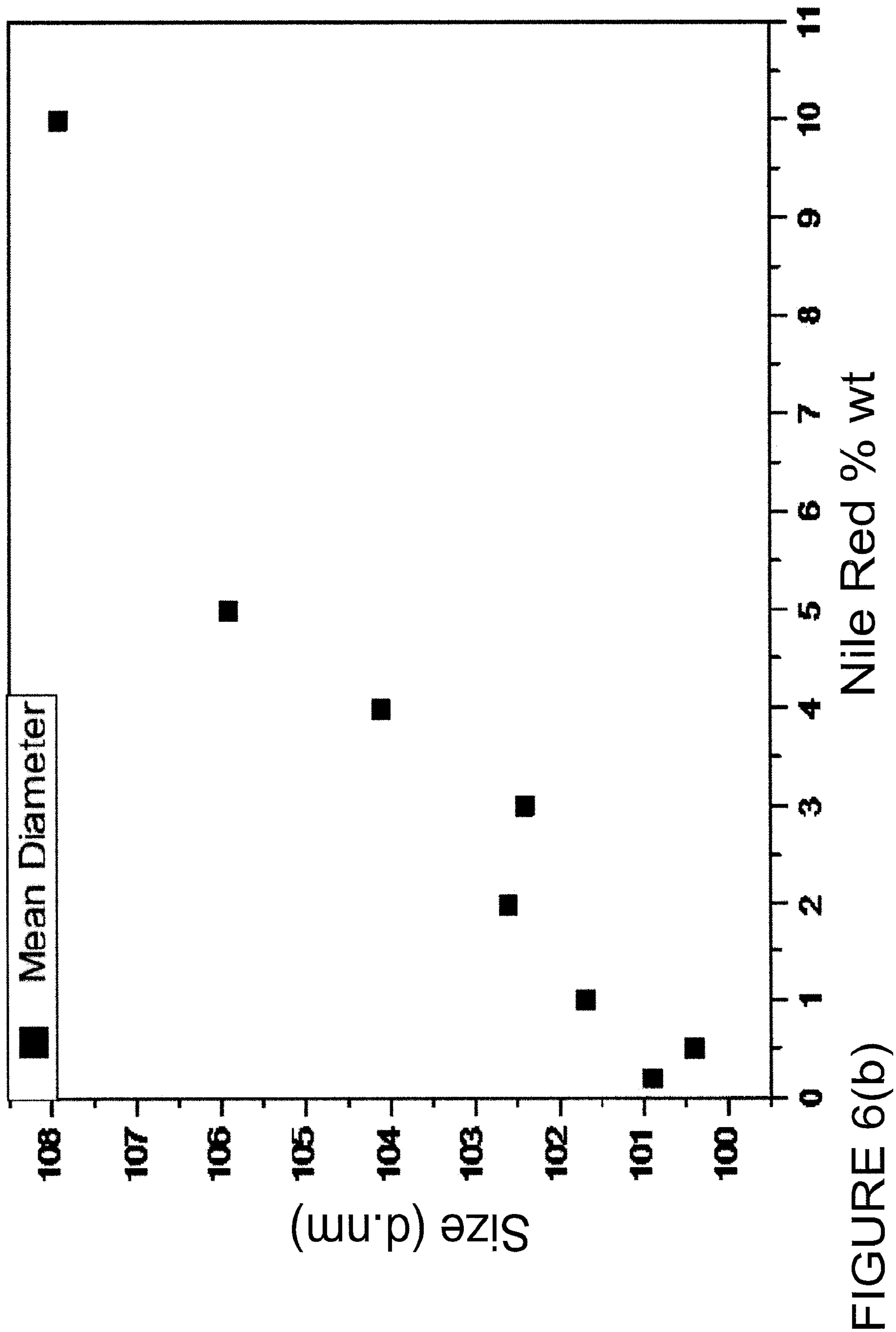
Figure 6C:
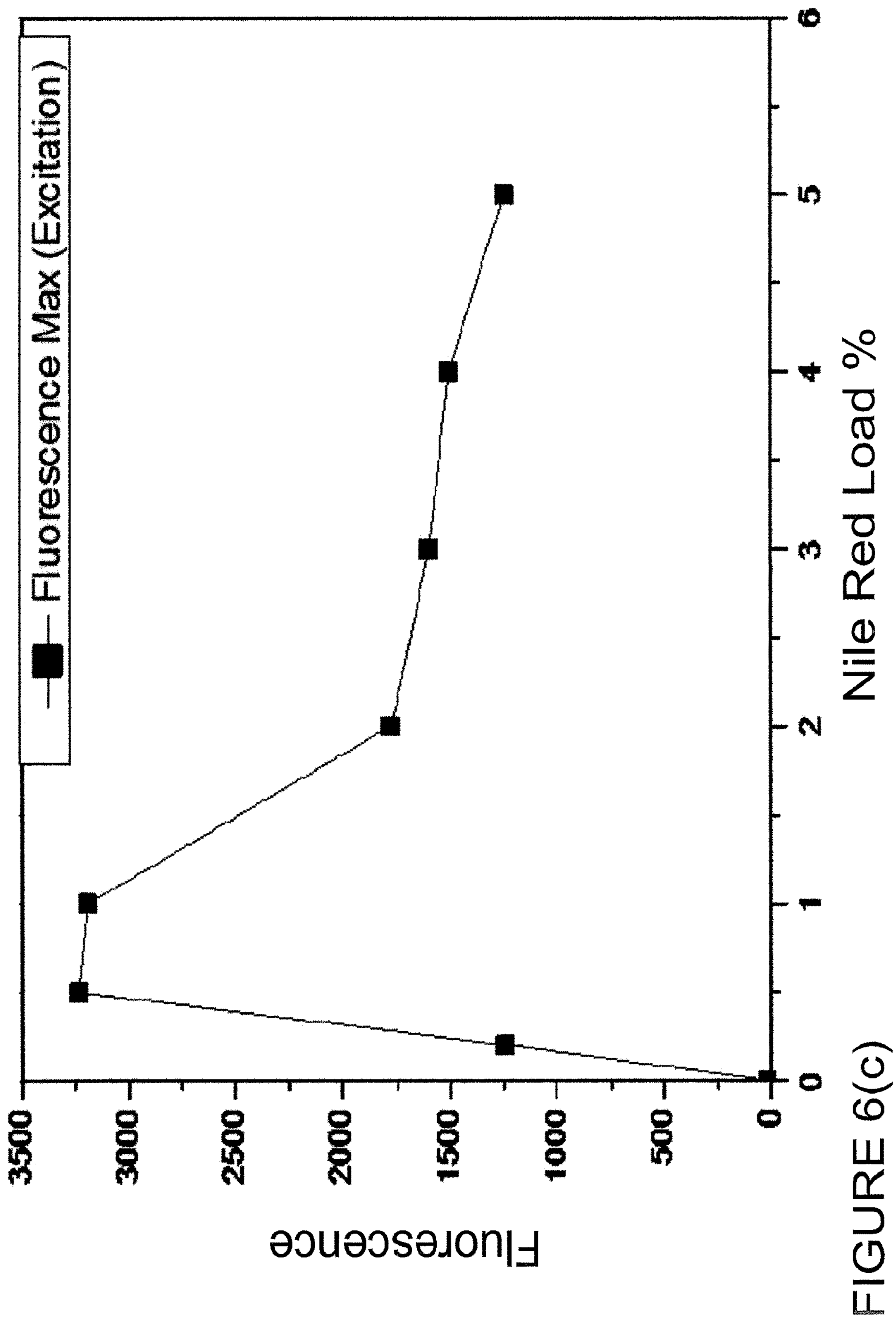
Figure 6D:
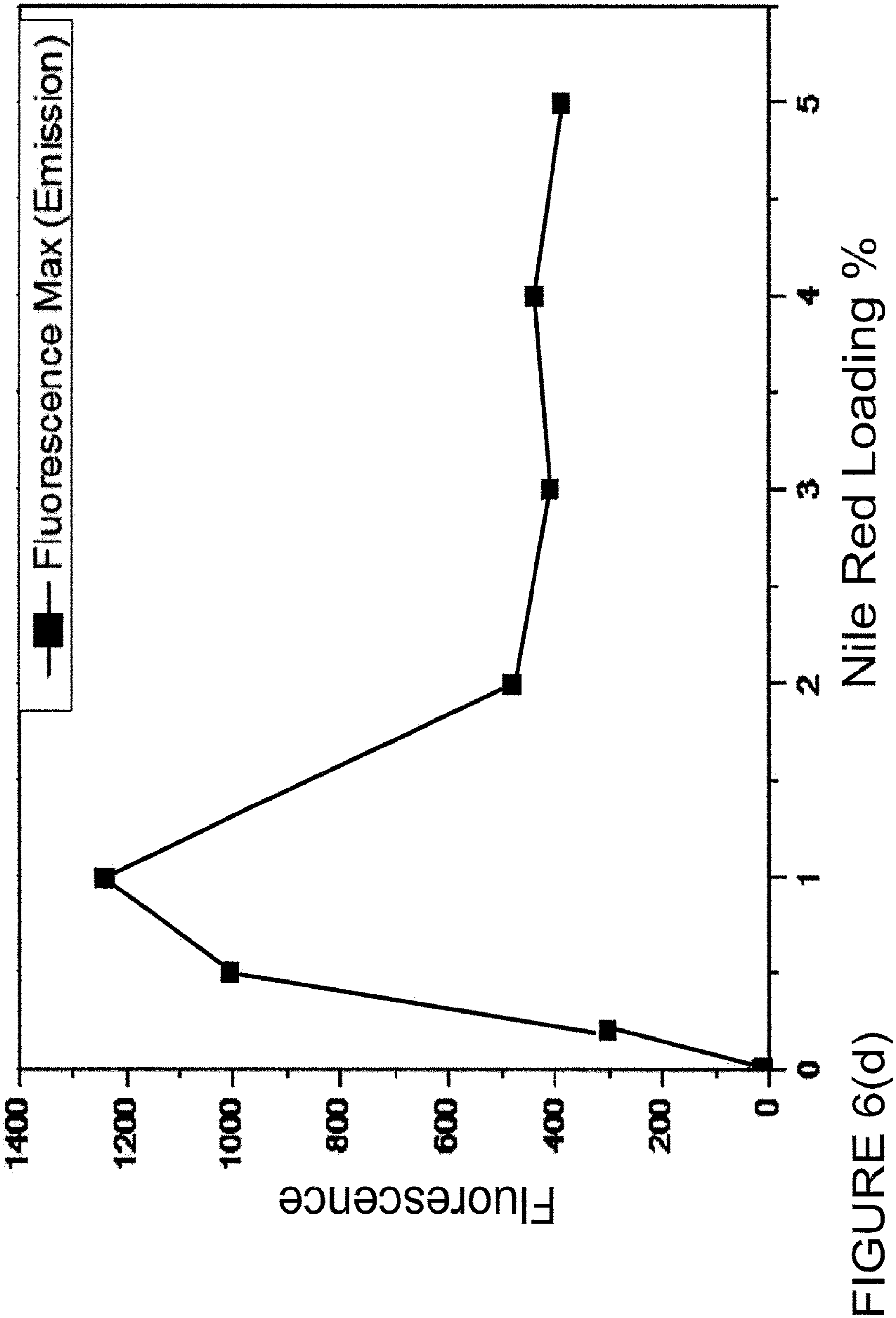
Figure 7:
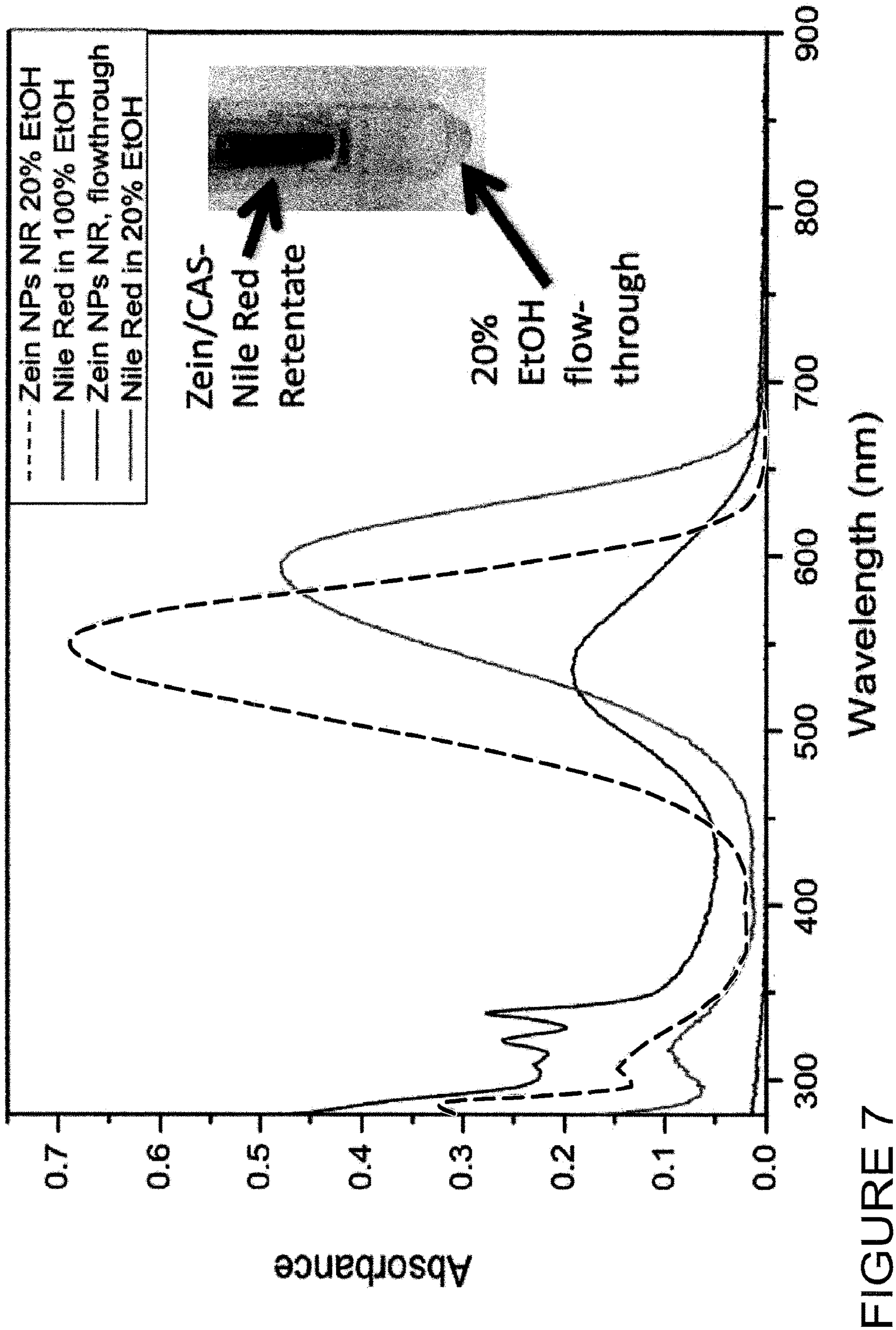
FIG. 7 illustrates Nile Red encapsulation effects and encapsulation efficiency according to some embodiments described herein.

The utility of an encapsulation method depends on its encapsulation capacity and efficiency for various compounds. Successful encapsulation of dyes with different physicochemical properties (FIG. 5) has been demonstrated (FIG. 6*a*) for Nile Red (log P 3.65, Log D 4.46, pH7.4), Pyrene (log P 5.17, Log D 4.92 pH7.4) and Methyl Red (log P 4.91, Log D 1.46 pH7.4). Due to its comparable hydrophobicity to CAI-1 (log P 4.35, log D 4.30 pH7.4), loading efficiency studies were conducted using Nile Red as model compound. Nile Red was encapsulated at 0.2%-5 wt. %. At 0.1% wt. Nile Red loading, the UV signal was below the detection limit, while at 10% wt. immediate aggregation of NPs was observed after FNP. Dye co-encapsulation with VitE-Ac at the core of zein/CAS NPs showed a red-shifted UV spectrum relative to free Nile Red solution in 100%, while the UV spectrum of free Nile Red in aqueous 20% EtOH showed a strong blue-shift (FIG. 7). This suggests the encapsulation of Nile Red into Zein/CASNitEA NPs. Encapsulation efficiency of Nile Red in Zn/CAS-VitE-Ac NPs was >98% for all stable formulations as determined by UV-Vis measurement of the flow through after centrifugal filtration (FIG. 7). With increasing Nile Red concentration in the core, the mean nanoparticle diameter increases (FIG. 6*b*). The florescence intensity is expected to increase with higher dye loading per particle. This can be seen in FIGS. 6(*c*) and 6(*d*)

for two different wavelengths (500 nm excitation, 690 nm emission) and core loadings of 0.2-1% wt. However, at dye content higher than 1% wt., the fluorescence intensity decreases, which suggests a dye-quenching effect. Fluorescence quenching can derive from physical proximity of individual molecules, and in this case, it suggests that Nile Red may preferentially accumulate in the hydrophobic VitE-Ac core.

Example 2—Composite Nanoparticles Stability and Redispersibility after Freeze-Drying 1. Preparation
a. Buffer: 0.150 g Sodium citrate, and 1.5 mg citric acid in 50 mL milliQ $H_2O$, adjusted to pH7.5 with 1M NaOH, 1M HCl, then 0.2 μm filtered.
b. MIVM Line-in:
  i. (1): 100% EtOH 2 mg/mL α-tocopherol (12 mL/min)
  ii. (2): Sodium citrate pH 7.5, 0.1M (36 mL/min)
  iii. (3): 60% EtOH of 11 mg/mL Zein+0.13 mg/mL F68 Pluronic (12 mL/min)
  iv. (4): Sodium citrate pH 7.5, 0.1M (36 mL/min)
c. Final NP concentration is 1.64 mg/mL in 20% EtOH.
d. NPs were either i) dialyzed against milliQ $H_2O$ using a cellulose dialysis tubing for 2 hours with one full buffer exchange at 1 hr.
e. Particles were kept in milliQ $H_2O$ 24 hrs before use at RT.
f. Freeze-drying excipient conditions:
  i. 10 mM $KH_2PO_4$ pH7.5
  ii. Sodium citrate buffer
  iii. Maltodextrin 8% wt. in 0.1M sodium citrate buffer pH 7.5
  iv. Maltodextrin 8% wt. in 10 mM $KH_2PO_4$ pH7.5
  v. Sucrose 8% wt. in 10 mM $KH_2PO_4$ pH7.5
  vi. Trehalose 8% wt. in 10 mM $KH_2PO_4$ pH7.5
  vii. Pluronic F68 0.16% wt. 10 mM $KH_2PO_4$ pH7.5
  viii. Maltodextrin 6% wt. in 0.1M sodium citrate buffer pH 7.5 and Pluronic F68 0.04% wt
  ix. Maltodextrin 6% wt. in 10 mM $KH_2PO_4$ pH7.5 and Pluronic F68 0.04% wt
  x. Sucrose 6% wt. in 10 mM $KH_2PO_4$ pH7.5 and F68 0.04% wt
  xi. Trehalose 6% wt. in 10 mM $KH_2PO_4$ pH7.5 and F68 0.04% wt
g. Samples were measured in liquid suspension (DLS) and frozen on dry ice the same day (within 3 hours), then set to lyophilize on tree freeze dryer (no precise temperature control)~100 mTorr for 72 hours. Samples were redispersed with milliQ water, to original volume prior to freeze-drying, shortly vortexed, and analysed by DLS.
2. Characterization of Particles
a. Dynamic light scattering: Used company recommended refractive index settings for protein particles (RI: 1.450; Absorption: 0.010) in water (RI: 1.330; Viscosity: 0.8872 cP, 25° C.). Using a Zetasizer® Nano-ZS (Malvern instruments, Malvern, UK), dynamic light scattering (DLS) size measurements were performed on samples directly after FNP and at a 10-fold dilution in milliQ water (final EtOH content: <2% v/v). Samples were analyzed at 25° C. using a detection angle of 173°. The reported size is the intensity-weighted average diameter as reported by the Malvern deconvolution software in Normal Mode analysis.

3. Results

Phosphate buffer above 10 mM is known to destabilize and aggregate zein colloidal particles. Zein was less stable in 10 mM $KH_2PO_4$ than in 0.1M sodium citrate. Additionally, freeze-concentration during lyophilisation likely increased the molarity of the phosphate buffer, which would further drive aggregation of zein. However, the excipient formulation (10) comprising, 6% wt. sucrose, 0.04% wt. Pluronic F68 was able to preserve zein nanoparticles during freeze-drying and resuspension. Stability of the formulation would likely be further increased by increasing sucrose content, and using sodium citrate buffer instead of $KH_2PO_4$.

In the case of sodium caseinate as stabilizer, because of the higher zeta potential of the resulting nanocomposites, NPs are stable during lyophilization and resuspension. Therefore, we demonstrate stability during lyophilization for a formulation (using PLURONIC F68 as surfactant) that is more challenging to stabilize during lyophilization and resuspension.

Example 3—Composite Nanoparticles Temperature Stability in Acidic Conditions

1. Preparation
a. Buffer: 0.150 g Sodium citrate, and 1.5 mg citric acid in 50 mL milliQ $H_2O$, adjusted to pH7.5 with 1M NaOH, 1M HCl, then 0.2 μm filtered.
b. MIVM Line-in:
  i. (1): 100% EtOH 2 mg/mL α-tocopherol (12 mL/min)
  ii. (2): Sodium citrate pH 7.5, 0.1M (36 mL/min)
  iii. (3): 60% EtOH of 11 mg/mL Zein+0.13 mg/mL F68 Pluronic (12 mL/min)
  iv. (4): Sodium citrate pH 7.5, 0.1M (36 mL/min)
c. Final NP concentration is 1.64 mg/mL in 20% EtOH.
d. NPs were dialyzed against milliQ $H_2O$ using a cellulose dialysis tubing for 2 hours with one full buffer exchange at 1 hr.
e. Particles were suspended in 0.1M HCl pH2.0 (simulating a stomach pH environment) and particles were subjected to a temperature ramp from 25° C. to 60° C., over a 2 hour period. NP size and particle count rate were measured continuously by DLS.
2. Characterization of particles
a. Dynamic light scattering: Used company recommended refractive index settings for protein particles (RI: 1.450; Absorption: 0.010) in water (RI: 1.330; Viscosity: 0.8872 cP, 25° C.). Using a Zetasizer® Nano-ZS (Malvern instruments, Malvern, UK), dynamic light scattering (DLS) size measurements were performed on samples directly after FNP and at a 10-fold dilution in milliQ water (final EtOH content: <2% v/v). Samples were analyzed at 25° C. using a detection angle of 173°. The reported size is the intensity-weighted average diameter as reported by the Malvern deconvolution software in Normal Mode analysis.

3. Results

The size of NPs were stable (diameter ~209 nm+/−6 nm) during the 2 hr temperature ramp from 25° C. to 60° C. in acidic conditions (0.01M HCl pH 2.0). Moreover, PDI remained stable over time during heat ramp to 60° C. as illustrated in FIG. 4. Mean particle diameter and PDI at temperatures 25° C. (206 nm, 0.045), 45° C. (210 nm, 0.005), and 60° C. (209 nm, 0.040) did not vary significantly.

Example 4—Composite Nanoparticle Stability in PBS when Pretreated with Dicarboxylic Acid 1. Preparation
   a. Buffer: 0.150 g Sodium citrate, and 1.5 mg citric acid in 50 mL milliQ $H_2O$, adjusted to pH7.5 with 1M NaOH, 1M HCl, then 0.2 μm filtered.
   b. MIVM Line-in:
      i. (1): 100% EtOH 2 mg/mL α-tocopherol (12 mL/min)
      ii. (2): Sodium citrate pH 7.5, 0.1M (36 mL/min)
      iii. (3): 60% EtOH of 11 mg/mL Zein+0.13 mg/mL F68 Pluronic (12 mL/min)
      iv. (4): Sodium citrate pH 7.5, 0.1M (36 mL/min)
   c. Final NP concentration is 1.64 mg/mL in 20% EtOH.
   d. NPs were dialyzed against milliQ $H_2O$ using a cellulose dialysis tubing for 2 hours with one full buffer exchange at 1 hr.
   e. Particles were suspended in 22% malic acid at pH13, and cross-linked for 2 hours at room temperature (protocol adapted from Reddy et al. 2009 AIChE "Alkai-catalyzed low temperature wet crosslinking of plant proteins using carboxylic acids").
2. Characterization of Particles
   a. Dynamic light scattering: Used company recommended refractive index settings for protein particles (RI: 1.450; Absorption: 0.010) in water (RI: 1.330; Viscosity: 0.8872 cP, 25° C.). Using a Zetasizer® Nano-ZS (Malvern instruments, Malvern, UK), dynamic light scattering (DLS) size measurements were performed on samples directly after FNP and at a 10-fold dilution in milliQ water (final EtOH content: <2% v/v). Samples were analyzed at 25° C. using a detection angle of 173°. The reported size is the intensity-weighted average diameter as reported by the Malvern deconvolution software in Normal Mode analysis.
3. Results Malic acid treated NPs retained size better in 1×PBS relative to untreated NPs, which aggregated within 5 min of being suspended in 1×PBS. Malic acid has previously shown to cross-link zein hydroxyl groups via intermediate cyclic anhydride on the acid catalyst that cross-links with the polymer/peptide (Reddy N et al. *Biotechnol Prog.* 2009). However, even malic acid treated particles aggregated over time in PBS.

| Particle Type | Size Dh (nm) | PDI |
|---|---|---|
| NPs in $H_2O$ | 174 | 0.023 |
| Malic acid treated | 316.5 | 0.061 |
| Malic acid treated in 1x PBS t = 0 | 282.3 | 0.203 |
| Malic acid treated in 1x PBS t = 30 | 516.2 | 0.255 |

Example 5—Size Control of Zein Nanoparticles, Various Formulations

Various FNP-MIVM formulations achieve a different range of nanoparticle size with low PDI.

1. Preparation
   a. Buffer: 0.150 g Sodium citrate, and 1.5 mg citric acid in 50 mL milliQ $H_2O$, adjusted to pH7.5 with 1M NaOH, 1M HCl, then 0.2 μm filtered.
   b. Formulation 1 (MIVM Line-in):
      i. (1): 100% EtOH 1 mg/mL α-tocopherol (12 mL/min)
      ii. (2): Sodium citrate pH 7.5, 0.1M (36 mL/min)
      iii. (3): 60% EtOH of 11 mg/mL Zein+0.4 mg/mL Pluronic F6+1.8 mg/mL D-Lysine (12 mL/min)
      iv. (4): Sodium citrate pH 7.5, 0.1M (36 mL/min)
   c. Formulation 2 (MIVM Line-in):
      i. (1): 100% EtOH (12 mL/min)
      ii. (2): Sodium citrate pH 7.5, 0.1M (36 mL/min)
      iii. (3): 60% EtOH of 11 mg/mL Zein, 2 wt % Pluronic F68
      iv. (4): Sodium citrate pH 7.5, 0.1M (36 mL/min)
   d. Formulation 3 (MIVM Line-in):
      i. (1): 100% EtOH 2 mg/mL α-tocopherol (12 mL/min)
      ii. (2): Sodium citrate pH 7.5, 0.1M (36 mL/min)
      iii. (3): 60% EtOH of 11 mg/mL Zein, 0.35 mg/mL Pluronic F68
      iv. (4): Sodium citrate pH 7.5, 0.1M (36 mL/min)
   e. Formulation 4 (MIVM Line-in):
      i. (1): 100% EtOH 1 mg/mL α-tocopherol (12 mL/min)
      ii. (2): Sodium citrate pH 7.5, 0.1M (36 mL/min)
      iii. (3): 60% EtOH of 11 mg/mL Zein, 0.35 mg/mL Pluronic F68, 1.6 mg/mL Malic Acid (12 mL/min)
      iv. (4): Sodium citrate pH 7.5, 0.1M (36 mL/min)
   f. NPs were either i) dialyzed agains milliQ $H_2O$ using a cellulose dialysis tubing for 2 hours with one full buffer exchange at 1 hr, or ii) stored as is (in 20% EtOH) at either RT or 4-8° C.
2. Characterization of particles
   a. Dynamic light scattering: Used company recommended refractive index settings for protein particles (RI: 1.450; Absorption: 0.010) in water (RI: 1.330; Viscosity: 0.8872 cP, 25° C.). Using a Zetasizer® Nano-ZS (Malvern instruments, Malvern, UK), dynamic light scattering (DLS) size measurements were performed on samples directly after FNP and at a 10-fold dilution in milliQ water (final EtOH content: <2% v/v). Samples were analyzed at 25° C. using a detection angle of 173°. The reported size is the intensity-weighted average diameter as reported by the Malvern deconvolution software in Normal Mode analysis.
   b. pH was measured

| | F-1 | F-2 | F-3 | F-4 |
|---|---|---|---|---|
| Size (nm) | 84 | 127 | 199 | 331 |
| PDI | 0.076 | 0.008 | 0.026 | 0.049 |

Results

As provided in the table above and FIG. 2, the FNP process using the MIVM mixer produced zein nanoparticle in with low polydispersity over a wide range of sizes. DLS measurements recorded mean diameters ranging from 80 nm-330 nm, and individual particles ranging from 40 nm-700 nm. The PDI remained below 0.1 for the formulations tested. Lysine has a pKa of 10.5 and is a basic residue. Formulation 1 was slightly basic, while Formulation 4 was slightly acidic. The charge of zein, as dependent on the pH of the solution, therefore impacts the final size of nanoparticles. The difference between formulation F-2 having no lipid core and F-3 is the inclusion of a Vitamin-E core (at 2 mg/mL).

Example 6—Inverse Zein Nanoparticles Precipitated into Ethanol

Zein is an amphiphilic biopolymer that can be precipitated against an aqueous stream or an organic stream. Zein is insoluble in pure EtOH. Instead of precipitating into aqueous environment, where the hydrophobic residues are predominantly on the particle interior, zein nanoparticles are precipitated into organic (EtOH) to form a predominantly hydrophilic particle interior with a hydrophobic exterior.

Preparation a. MIVM Line-in:
  i. (1): 100% EtOH (12 mL/min)
  ii. (2): 100% EtOH (36 mL/min)
  iii. (3): 60% EtOH of 11 mg/mL Zein (12 mL/min)
  iv. (4): 100% EtOH (36 mL/min)
b. Final NP concentration is 1.375 mg/mL in 95% EtOH.
c. NPs were diluted 10-fold in 100% EtOH and measured using DLS.

Characterization of Particles b. Dynamic light scattering: Used company recommended refractive index settings for protein particles (RI: 1.450; Absorption: 0.010) in ethanol (RI: 1.360; Viscosity: 1.095 cP, 25° C.). Using a Zetasizer® Nano-ZS (Malvern instruments, Malvern, UK), dynamic light scattering (DLS) size measurements were performed on samples directly after FNP and at a 10-fold dilution in 100% EtOH (final aqueous content: <0.5% v/v). Samples were analyzed at 25° C. using a detection angle of 173°. The reported size is the intensity-weighted average diameter as reported by the Malvern deconvolution software in Normal Mode analysis.

Results

Figure 8:
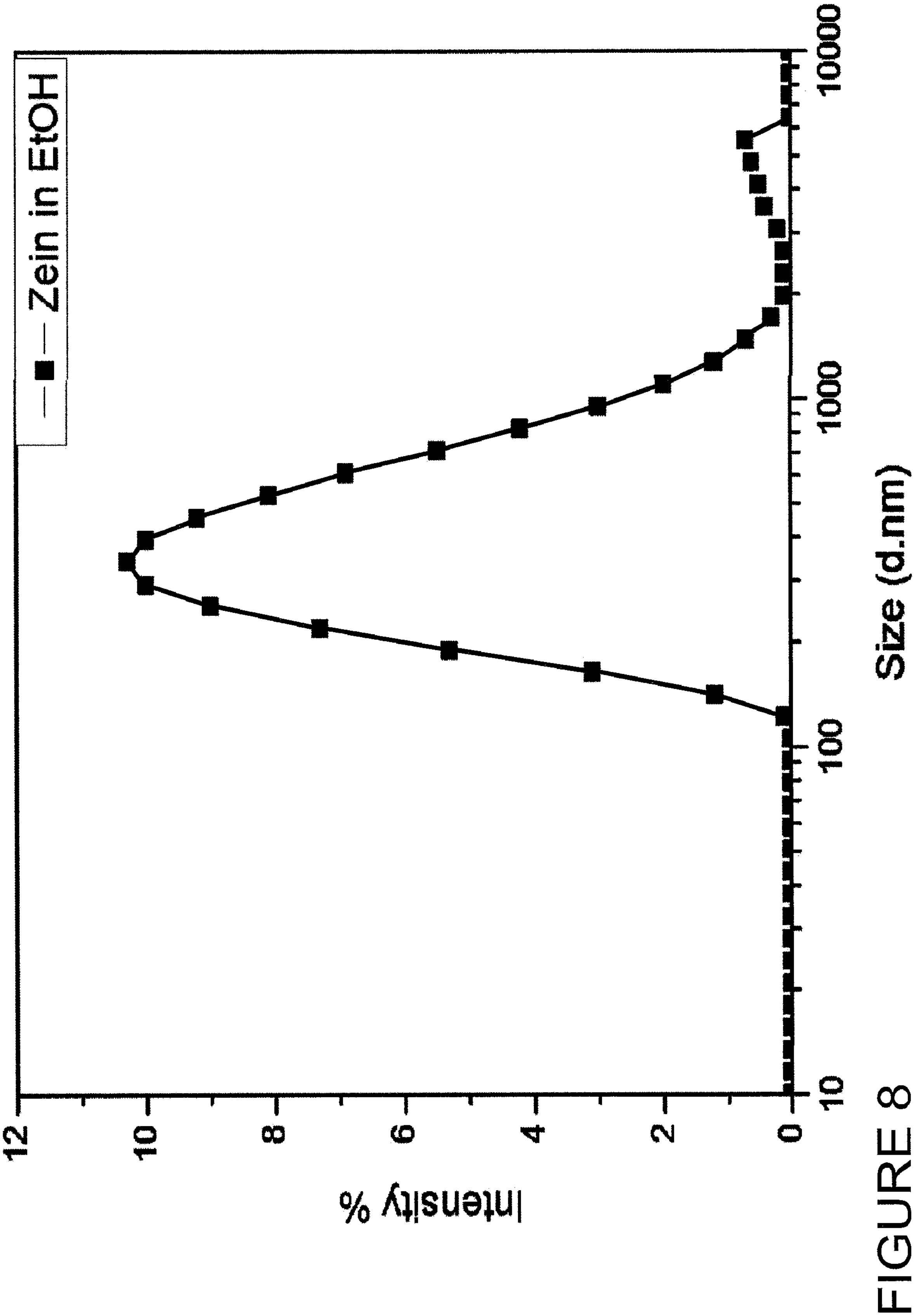
FIG. 8 illustrates zein nanoparticle size distribution according to some embodiments described herein, the zein nanoparticles having a hydrophilic interior and hydrophobic exterior.

Inverse zein nanoparticles were formed using the MIVM. The high super saturation and flow rates allow for nucleation and growth of NPs at 95% EtOH concentration within the mixer. Without stabilizer, zein particles had a mean diameter of 418 nm+/−36 nm, and a polydispersity of 0.242+/−0.013 as illustrated in FIG. 8.

Example 7—Composite Nanoparticle Bioactivity

To minimize loss of precious actives, it was important to ensure minimal free drug in solution after FNP. To identify the highest loading efficiency for CAI-1 into Zn/CAS-VitE-Ac NPs, CAI-1 encapsulation was tested for 1×, 2×, 3×-fold mass of NPs at a constant amount of drug. Compositions and flow rates for the nanocarrier species in FIG. 9(*a*) are provided in FIG. 19.

Figure 9A:
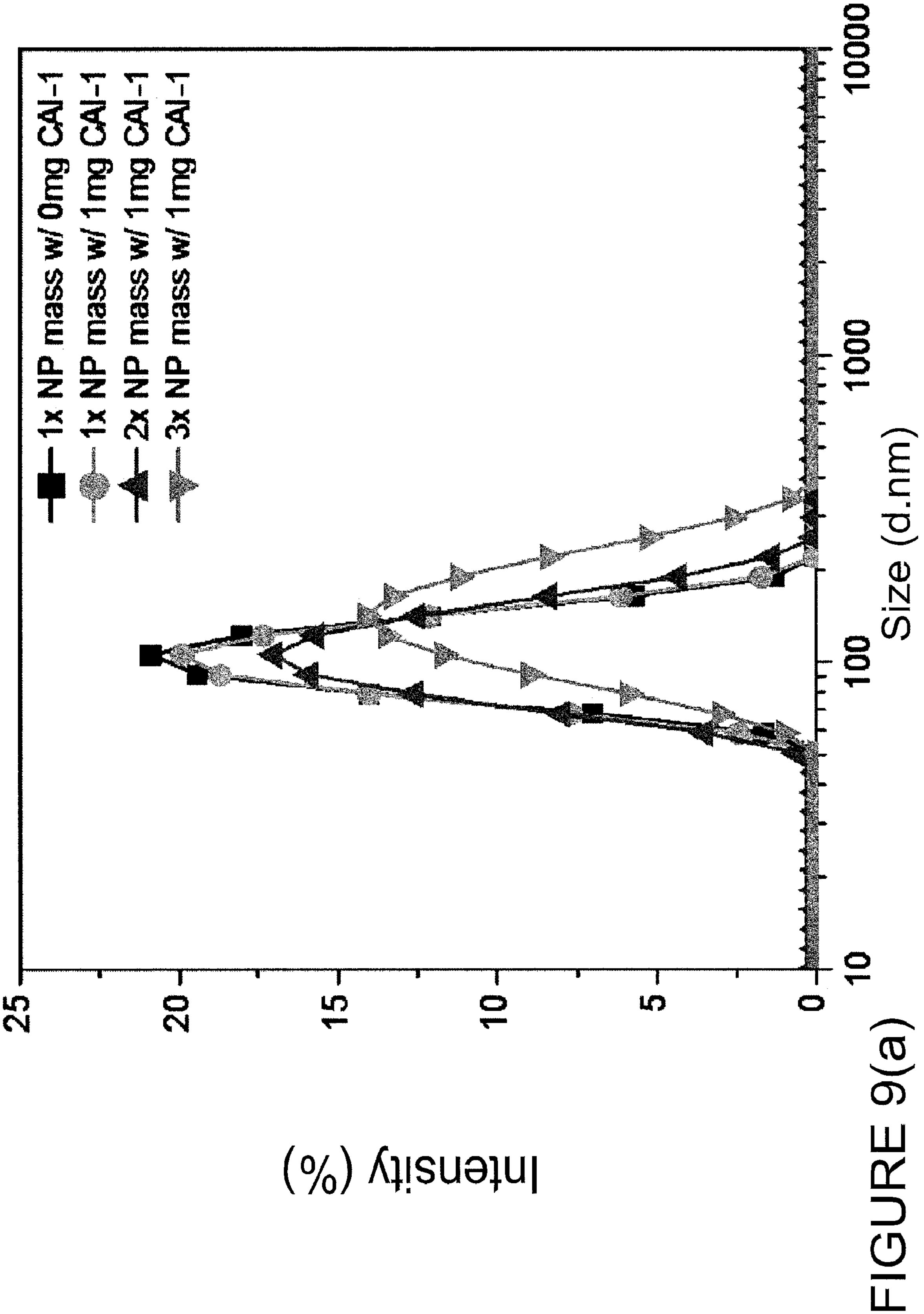
FIG. 9(*a*) illustrates effect of composite nanoparticle size and PDI of two-fold and three-fold protein and VitE-Ac masses at constant CAI-1 content according to some embodiments described herein.
Figure 9B:
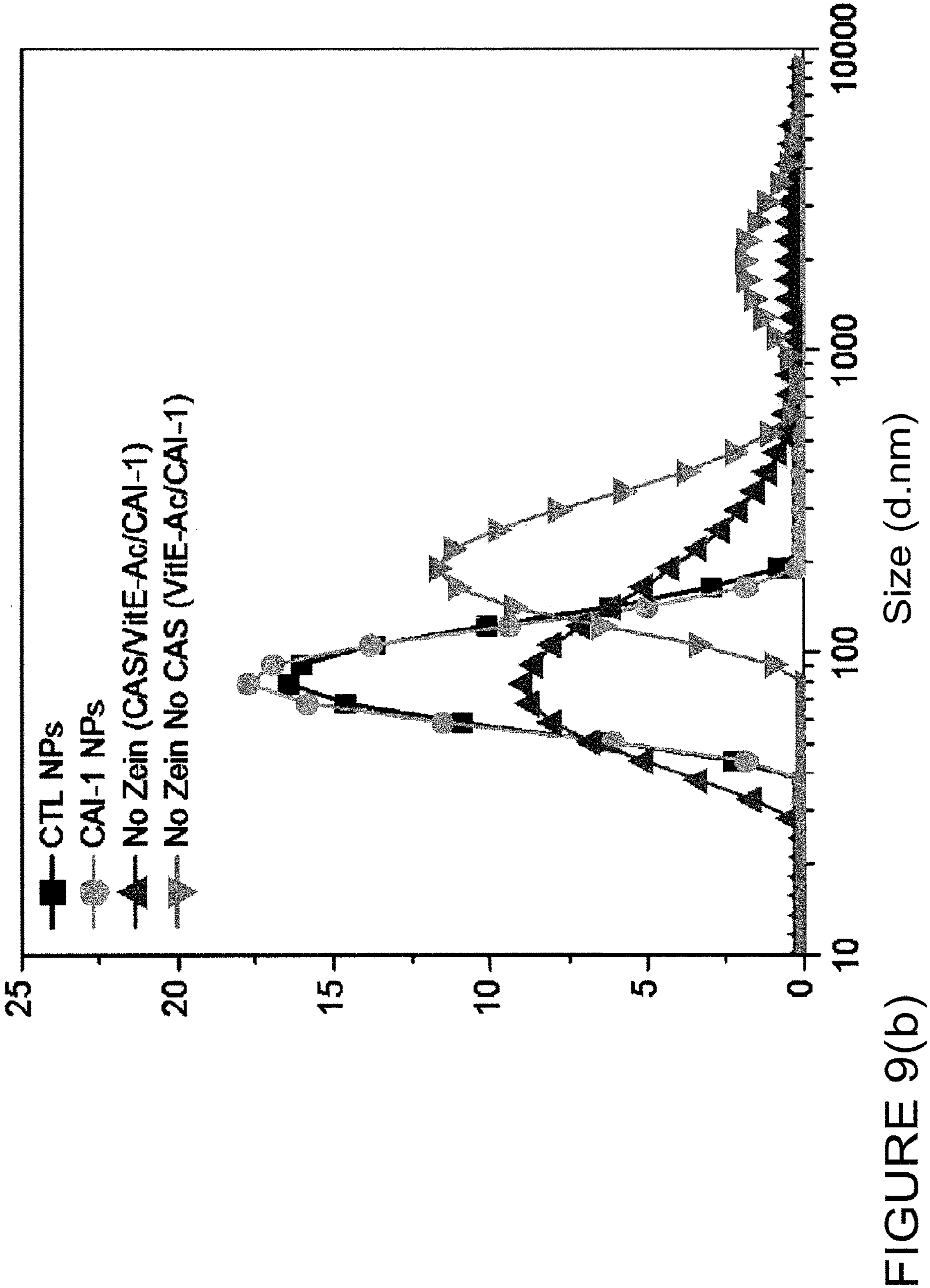

The encapsulation of CAI-1 did not impact the size or PDI of NPs. Changes in size and PDI could only be observed for the three-fold protein per amount of drug formulation (FIG. 9*a*). All formulations showed similarly high encapsulation as determined by in vitro bioactivity assay (data not shown). All parts of the formulation were necessary for the formation of nanoparticles with defined size. NPs that lacked either zein, or zein and casein did not form nanoparticles with controlled size (FIG. 9*b*). FNP of CAI-1 alone yielded a polydisperse emulsion, which then agglomerated and settled out over time. There was no apparent effect of CAI-1 or NPs on the growth of cells during the time tested (FIG. 10*a*).

The bioactivity of blank Zein/CAS/VitEA particles was not detectable (FIG. 10*b*). The retentate of NPs containing CAI-1 showed high anti-bacterial activity, and was similarly efficacious as free drug in DMSO, and unfiltered NPs containing CAI-1 (FIG. 10*b*). The flow-through after centrifugal filtration can be regarded as a correlate for encapsulation efficiency of CAI-1. Bioactivity of the flow through was observed only at very high concentrations, approximately 1,000-10,000-fold higher than CAI-1 NPs. This suggests better than 98% encapsulation efficiency of CAI-1 during FNP. These data suggest that CAI-1 loaded Zein/CAS/VitEA NPs prepared by FNP, are a feasible and efficacious low-cost GRAS therapeutic with potential as efficacious cholera prophylactic.

Example 8—Zein Co-Precipitation with Biomolecules, including Nucleic Acids and Proteins DNA-Zein Nanocarrier Preparation a. Buffer: 0.150 g Sodium citrate, and 1.5 mg citric acid in 50 mL milliQ $H_2O$, adjusted to pH7.5 with 1M NaOH, 1M HCl, then 0.2 μm filtered.
b. MIVM Line-in:
  i. (1): 62.5 m/mL Salmon Sperm DNA in 0.1M sodium citrate buffer pH7.5 (12 mL/min)
  ii. (2): $dH_2O$ (36 mL/min)
  iii. (3): 60% EtOH of 12 mg/mL Zein (12 mL/min)
  iv. (4): $dH_2O$ (36 mL/min)

Particles were collected after one-step Flash Nanoprecipitation using the MIVM geometry.

BSA-Zein Nanocarrier Preparation c. Buffer: 0.150 g Sodium citrate, and 1.5 mg citric acid in 50 mL milliQ $H_2O$, adjusted to pH7.5 with 1M NaOH, 1M HCl, then 0.2 μm filtered.
d. MIVM Line-in:
  i. (1): 0.1 mg/mL BSA-FITC in 0.1M sodium citrate buffer pH7.5 (12 mL/min)
  ii. (2): $dH_2O$ (36 mL/min)
  iii. (3): 60% EtOH of 12 mg/mL Zein (12 mL/min)
  iv. (4): $dH_2O$ (36 mL/min)

Characterization of Particles a. Dynamic light scattering: Used company recommended refractive index settings for protein particles (RI: 1.450; Absorption: 0.010) in water (RI: 1.330; Viscosity: 0.8872 cP, 25° C.). Using a Zetasizer® Nano-ZS (Malvern instruments, Malvern, UK), dynamic light scattering (DLS) size measurements were performed on samples directly after FNP and at a 10-fold dilution in milliQ water (final EtOH content: <2% v/v). Samples were analyzed at 25° C. using a detection angle of 173°. The reported size is the intensity-weighted average diameter as reported by the Malvern deconvolution software in Normal Mode analysis.
b. Zeta potential: Using a Zetasizer Nano-ZS (Malvern instruments, Malvern, U.K.), dynamic light scattering (DLS) size measurements were performed on samples after FNP and dialysis. For zeta potential measurements, samples were diluted with 20 mM sodium chloride to a 10 mM salt concentration.

Results

Figure 11:
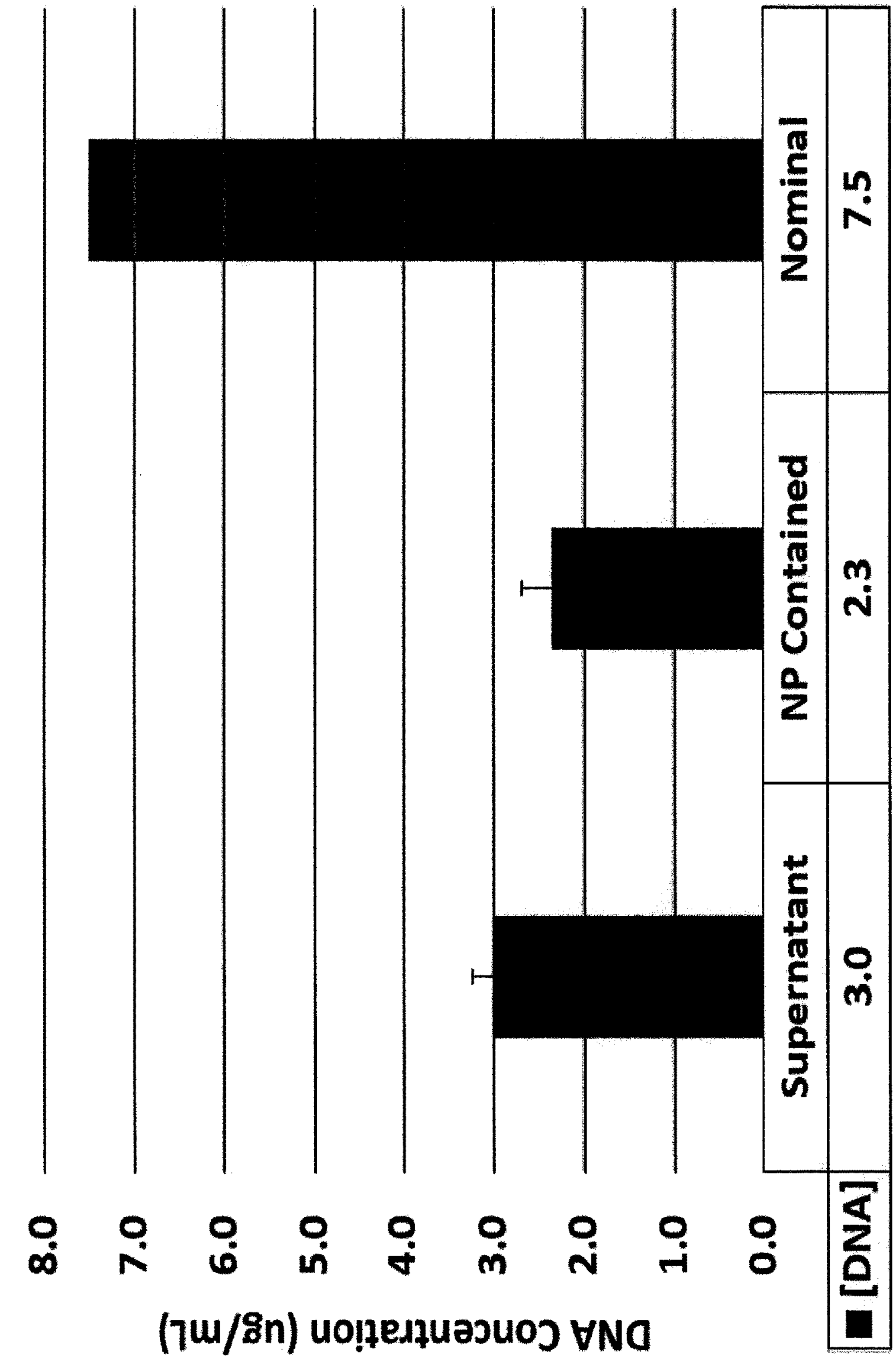
FIG. 11 illustrates DNA encapsulation and loading efficiency into zein containing colloids according to some embodiments described herein.

Zein combines with salmon sperm DNA during FNP to form 152 nm particles with low polydispersity (PDI=0.062). Moreover, the formed nanocarriers incorporated 4.7 μg of DNA per 1 mg of zein at solution pH of 7.5, zein feed concentration of 12 mg/ml and relative mass ratio zein:DNA of 200:1. FIG. 10 provides additional parameters of DNA encapsulation by zein. FIG. 11 illustrates DNA encapsulation and loading efficiency into zein containing colloids according to some embodiments described herein.

Figure 12:
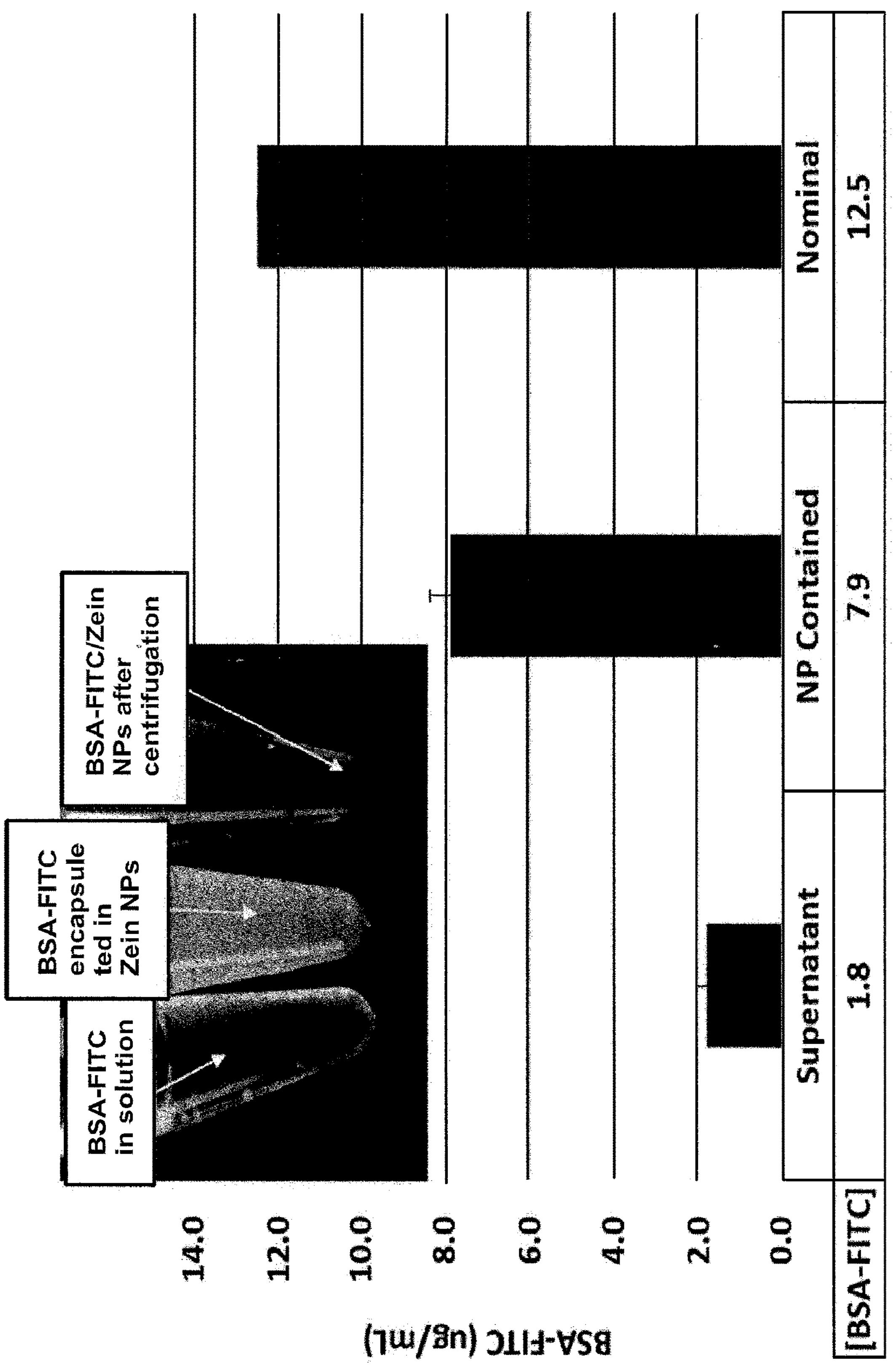
FIG. 12 illustrates BSA-FTIC encapsulation and loading efficiency into zein containing colloids according to some embodiments described herein.

Zein combines with BSA-FITC during FNP to form 194 nm particles with low PDI=0.073. Additionally, the formed nanocarriers incorporated 7.5 μg of BSA-FITC per 1 mg of zein at solution pH of 7.5, zein feed concentration of 12 mg/ml and relative mass ratio zein:BSA-FITC of 16:1. FIG. 12 illustrates BSA-FTIC encapsulation and loading efficiency into zein containing colloids according to some embodiments described herein.

Figure 13:
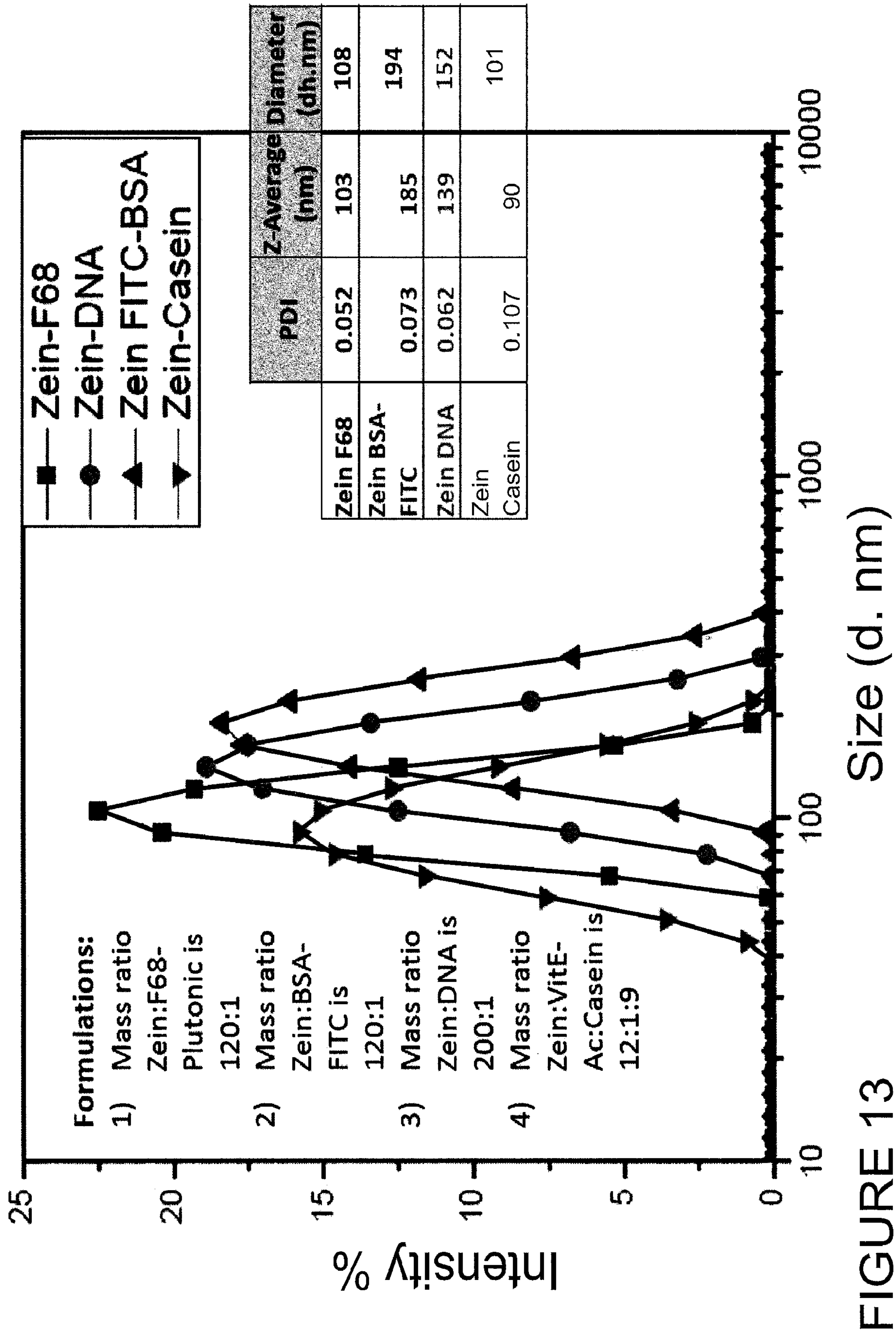
FIG. 13 illustrates the effect of additives or stabilizers, having an isoelectric point below solution pH, on the size and PDI of resulting colloids according to some embodiments described herein.
Figure 14:
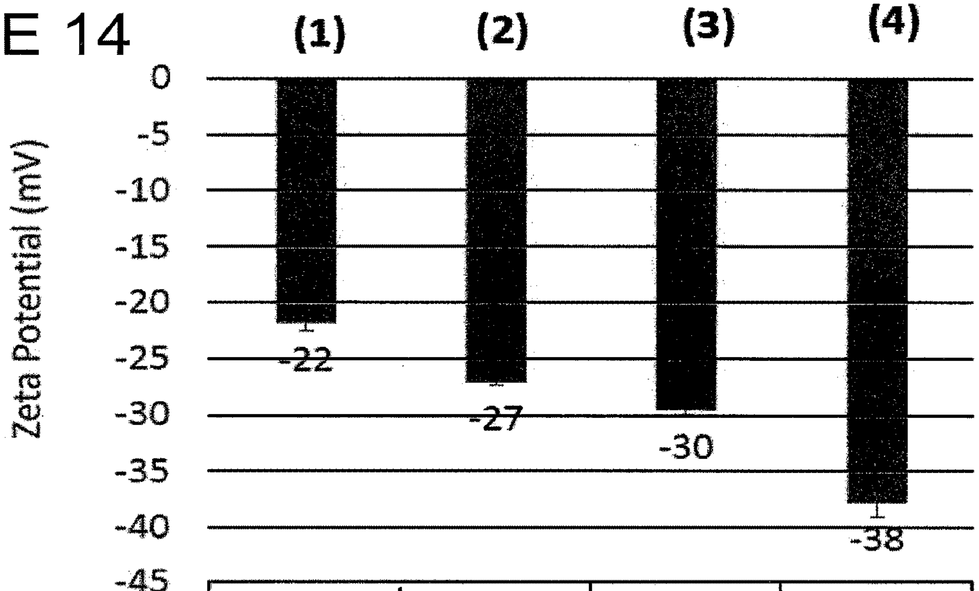
FIG. 14 illustrates the effect of additives or stabilizers, having an isoelectric point below solution pH, on the zeta potential of the resultant nanocarrier colloids according to some embodiments described herein.

FIG. 13 illustrates the effect of additives or stabilizers, having an isoelectric point below solution pH, on the size and PDI of resulting colloids according to some embodiments described herein. FIG. 14 illustrates the effect of additives or stabilizers, having an isoelectric point below solution pH, on the zeta potential of the resultant nanocarrier colloids according to some embodiments described herein.

Example 9—Zein Shell, No Core Nanoparticles, Will Encapsulate Negatively Charged Biomolecules, Such as DNA or RNA Rationale: The isoelectric point of alpha-zein occurs at pH 6.8, and the isoelectric point of DNA occurs at approximately pH 5.0. At pH 5.5, zein is positively charged and DNA (and RNA) is negatively charged. Based on opposite net charge, the encapsulation of DNA (and RNA) into zein will be enhanced. The polar side chains on zein will interact with DNA. This can be true also at other pH ranges that are higher or lower than pH6.0. The resulting particles, will be charge stabilized, in that DNA (and RNA) will act in a similar fashion as sodium caseinate, that when combined with zein, alters the overall-zeta potential of the construct (nanoparticle), which will afford colloidal stability at physiologic conditions based on electrostatics. These formulations may include other surfactants. Ratios of zein:DNA and zein:RNA (and versions thereof, such as but not limited to: pDNA (plasmids), mRNA, siRNA, etc.) of 100:1 to 250:1 are expected to provide best particle formation propensity.

1. Preparation
a. Buffer 1: 0.150 g Sodium citrate, and 1.5 mg citric acid in 50 mL milliQ $H_2O$, adjusted to pH 5.5 (but may range from pH 3.0 to pH 7.5) with 1M NaOH, 1M HCl, then 0.2 μm filtered.
b. Buffer 2: 10 mM Tris, 1 mM EDTA, pH 6.0 (but may range from pH 5.5 to pH 7.5)
c. MIVM Line-in:
i. (1): 100% EtOH (12 mL/min; but may range from 2 ml/min to 12 mL/min)
ii. (2): Sodium citrate pH 5.5, 0.1M (36 mL/min; but may range from 2 mL/min to 36 mL/min)
iii. (3): 70% EtOH, pH 5.5 of 12 mg/mL Zein (12 mL/min; but may range from 2 ml/min to 12 mL/min)
iv. (4): 15-40 ug DNA/mL (best 25 ug DNA/mL) Tris-EDTA pH 6.0, 0.01M (36 mL/min; but may range from 2 mL/min to 36 mL/min)
d. The resultant solution is adjusted to pH10, using 1M NaOH, 1M HCl, and is then dialyzed against milliQ $dH_2O$ pH10 for 2 hours with 1 complete buffer change.
2. Characterization of particles
a. Dynamic light scattering: Will use company recommended refractive index settings for protein particles (RI: 1.450; Absorption: 0.010) in water (RI: 1.330; Viscosity: 0.8872 cP, 25° C.). Using a Zetasizer® Nano-ZS (Malvern instruments, Malvern, UK), dynamic light scattering (DLS) size measurements will be performed on samples directly after FNP and at a 10-fold dilution in milliQ water (final EtOH content: <2% v/v). Samples will be analyzed at 25° C. using a detection angle of 173°. The reported size will be the intensity-weighted average diameter as reported by the Malvern deconvolution software in Normal Mode analysis.
3. Results
a. The expected zeta potential of zein encapsulated DNA (and RNA) at pH 10 is approximately −70 mV. This will impart colloidal stability based on charge.
b. Particles with zein:DNA ratios of 100:1 to 250:1 are expected to be colloidally stable in 1×PBS (pH7.4) for 3 hours or longer.
c. Encapsulation efficiencies are expected to average about 40% (milligram DNA per gram of zein) but may be higher than 60%, and lower than 30%.

Example 10—Zein Shell, No Co-Core Nanoparticles, Encapsulating Proteins (>40 amino acids) and Peptides (<40 amino acids) by Side-Group Interactions Rationale: Zein can be used to encapsulate proteins (>40 amino acids) and peptides (<40 amino acids) using FNP. One possible application is the protection of enzymes from degrading conditions in the GI tract. For example, catalase (protein; pI pH 5.4; Samejima et al. 1962) or superoxide dismutase (protein; pI pH 4.95; Bannister et al. 1971) have been encapsulated using conventional zein coacervation method by magnetic stirring (Sugmun Lee et al *Int. J. Pharm* 2013). The synthetic peptide Desmopressin used as hematologic agent (log P −5.82, log $D_{pH7.4}$ −7.34; amides, amines, hydroxyl) has been encapsulated in zein. Here, the driving force for encapsulation is not net hydrophobicity or net charge of the molecule, but interactions of protein or peptide side groups with the side groups of zein. We can encapsulate proteins using the herein presented FNP method.

1. Preparation
a. Buffer 1: 0.150 g Sodium citrate, and 1.5 mg citric acid in 50 mL milliQ $H_2O$, adjusted to pH 7.5 (but may range from pH 6.0 to pH 8.0) with 1M NaOH, 1M HCl, then 0.2 μm filtered.
b. MIVM Line-in:
i. (1): 100% EtOH (12 mL/min; but may range from 2 ml/min to 12 mL/min)
ii. (2): Sodium citrate pH 7.5, 0.1M (36 mL/min; but may range from 2 mL/min to 36 mL/min)
iii. (3): 60% EtOH of 12 mg/mL Zein (may range from 5 mg/mL to 15 mg/mL)+0.15 mg/mL F68 Pluronic (or TPGS; might range from 0.10 mg/mL to 3 mg/mL) at a flow rate of 12 mL/min (but may range from 2 mL/min to 12 mL/min)
iv. (4): 10-40 μg protein/mL in sodium citrate pH 7.5, 0.1M (36 mL/min; but may range from 2 mL/min to 36 mL/min).
c. NPs will be dialyzed against milliQ $H_2O$ using a cellulose dialysis tubing for 2 hours with one full buffer exchange at 1 hr.
2. Characterization of particles
a. Dynamic light scattering: Will use company recommended refractive index settings for protein particles (RI: 1.450; Absorption: 0.010) in water (RI: 1.330; Viscosity: 0.8872 cP, 25° C.). Using a Zetasizer® Nano-ZS (Malvern instruments, Malvern, UK), dynamic light scattering (DLS) size measurements will be performed on samples directly after FNP and at a 10-fold dilution in milliQ water (final EtOH content: <2% v/v). Samples will be analyzed at 25° C. using a detection angle of 173°. The reported size will be the intensity-weighted average diameter as reported by the Malvern deconvolution software in Normal Mode analysis.

3. Results a. Particles are expected to have a mean diameter of 180 nm, but may range from 90 nm to 400 nm.

b. Particles are expected to be stable in low ionic aqueous buffers, an approximate pH range from pH 2.0 to pH 9.0, and milliQ $H_2O$.

c. Encapsulation efficiencies are expected to average about 40% (milligram protein per gram of zein) but may be higher than 60%, and lower than 30%.

Example 11—Zein Shell, No Co-Core Nanoparticles, Will Encapsulate Small Molecules with Charged Groups Rationale: Zein can be used to encapsulate small molecules with charged groups, and with or without a net dipole moment using FNP. For example, the anti-inflammatory drug Mesalazine (MW 153.1 g/mol; log P 0.46, log $D_{pH7.4}$ −1.98; primary amine, hydroxyl, carboxylic acid) has been encapsulated into microparticles using conventional zein coacervation method (Esther Lau et al. *Pharmaceutics* 2013). Here, the driving force for encapsulation is not net hydrophobicity or net charge of the molecule, but interactions of charged functional groups on the small molecule with the side groups of zein. We can encapsulate proteins using the herein presented FNP method.

1. Preparation a. Buffer 1: 0.150 g Sodium citrate, and 1.5 mg citric acid in 50 mL milliQ $H_2O$, is adjusted to pH 7.5 (but may range from pH 6.0 to pH 8.0) with 1M NaOH, 1M HCl, then 0.2 μm filtered.

b. MIVM Line-in:

i. (1): 100% EtOH (12 mL/min; but may range from 2 ml/min to 12 mL/min)

ii. (2): Sodium citrate pH 7.5, 0.1M (36 mL/min; but may range from 2 mL/min to 36 mL/min)

iii. (3): 60% EtOH of 12 mg/mL Zein (may range from 5 mg/mL to 15 mg/mL)+0.15 mg/mL F68 Pluronic (or TPGS; might range from 0.10 mg/mL to 3 mg/mL) at a flow rate of 12 mL/min (but may range from 2 mL/min to 12 mL/min)

iv. (4): 1 mg molecule/mL (but may range from 0.01 mg/mL to 2 mg/mL) in sodium citrate pH 7.5, 0.1M (36 mL/min; but may range from 2 mL/min to 36 mL/min)

2. Characterization of Particles a. Dynamic light scattering: Will use company recommended refractive index settings for protein particles (RI: 1.450; Absorption: 0.010) in water (RI: 1.330; Viscosity: 0.8872 cP, 25° C.). Using a Zetasizer® Nano-ZS (Malvern instruments, Malvern, UK), dynamic light scattering (DLS) size measurements will be performed on samples directly after FNP and at a 10-fold dilution in milliQ water (final EtOH content: <2% v/v). Samples will be analyzed at 25° C. using a detection angle of 173°. The reported size will be the intensity-weighted average diameter as reported by the Malvern deconvolution software in Normal Mode analysis.

3. Results a. Particles are expected to have a mean diameter of 120 nm, but may range from 80 nm to 400 nm.

b. Particles are expected to be stable in low ionic aqueous buffers, an approximate pH range from pH 2.0 to pH 9.0, and milliQ $H_2O$.

c. If sodium caseinate is used as surfactant, particles will be stable in physiologic buffer conditions for at least 3 hours.

d. Encapsulation efficiencies are expected to average about 10% (milligram molecule per gram of zein) but may be higher than 30%, and lower than 5% wt/wt.

Various embodiments of the invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the invention.

The invention claimed is:

1. A method of preparing a composite nanoparticle composition comprising:

providing a zein solution stream;

providing an organic solvent fluid stream comprising at least one additive; and providing at least one buffer fluid stream, wherein the zein solution stream, organic solvent fluid stream and buffer fluid stream are separately delivered to a chamber for mixing at one or more rates sufficient to flash precipitate composite nanoparticles including the additive encapsulated by a shell comprising the zein, wherein the additive is selected from the group consisting of a pharmaceutical composition, nutraceutical composition, food composition, beverage composition, agro active composition, taste-masking composition, biomolecular composition, personal care composition and cosmetic composition, and wherein the composite nanoparticles exhibit a polydispersity less than 0.3 in PBS buffer for a time period of at least 5 hours.

2. The method of claim 1, wherein the composite nanoparticles have an average size of 10 nm to 500 nm.

3. The method of claim 2, wherein the composite nanoparticles exhibit a polydispersity of less than 0.15.

4. The method of claim 1, wherein the organic solvent fluid stream comprises a plurality of additives.

5. The method of claim 4, wherein the plurality of additives are encapsulated by the shell comprising zein.

6. The method of claim 1, wherein the zein solution stream, organic solvent fluid stream and buffer fluid stream are simultaneously mixed in the chamber.

7. The method of claim 1, wherein zein solution stream, organic solvent fluid stream and buffer fluid stream are delivered to the chamber by independent feed lines.

8. The method of claim 1, wherein the one or more rates is at least 10 mL/min.

9. The method of claim 8, wherein the zein solution stream and the organic solvent fluid stream are delivered at a rate of 10-20 mL/min, and the buffer fluid stream is delivered at a rate of 30-40 mL/min.

10. The method of claim 1, wherein the zein solution stream comprises zein solubilized in a hydroalcoholic solution.

11. The method of claim 10, wherein the zein solution stream further comprises one or more stabilizers.

12. The method of claim 11, wherein the stabilizers comprise one or more surfactants.

13. The method of claim 11, wherein the one or more stabilizers are incorporated into or onto the composite nanoparticles.

14. The method of claim 13, wherein the one or more stabilizers are encapsulated by or adsorbed onto the shell comprising the zein.

15. The method of claim 13, wherein the one or more stabilizers are incorporated in or adsorbed onto the shell comprising the zein.

16. The method of claim 13, wherein the one or more stabilizers are encapsulated by the shell and incorporated in the shell comprising the zein.

17. The method of claim 1, wherein the buffer fluid stream comprises one or more stabilizers.

18. The method of claim 17, wherein the one or more stabilizers comprise casein.

19. The method of claim 1, wherein the additive is present in the composite nanoparticles in an amount of 0.1-60 weight percent.

20. The method of claim 1, further comprising extracting organic solvent from the nanoparticle composition for reuse in preparation of additional composite nanoparticles.

21. The method of claim 1 having an additive encapsulation efficiency of 40-100 percent.

22. The method of claim 21, wherein the additive encapsulation efficiency is 70 to 95 percent.

23. The method of claim 1, wherein the organic solvent is selected from the group consisting of ethanol, tetrahydrofuran, dimethylsulfoxide, and dimethylformamide.

24. A method of preparing a composite nanoparticle composition comprising:

providing a zein solution stream;

providing an organic solvent fluid stream comprising at least one additive; and providing at least one buffer fluid stream, wherein the zein solution stream, organic solvent fluid stream and buffer fluid stream are separately delivered to a chamber for mixing at one or more rates sufficient to flash precipitate composite nanoparticles including the additive encapsulated by a shell comprising the zein, wherein encapsulation efficiency of the additive is 90 percent to 100 percent.

25. A method of preparing a composite nanoparticle composition comprising:

providing a zein solution stream;

providing an organic solvent fluid stream comprising at least one additive; and providing at least one buffer fluid stream, wherein the zein solution stream, organic solvent fluid stream and buffer fluid stream are separately delivered to a chamber for mixing at one or more rates sufficient to flash precipitate composite nanoparticles including the additive encapsulated by a shell comprising the zein, wherein the additive is present in the composite nanoparticles in an amount of 1 to 20 weight percent.

26. A method of preparing a composite nanoparticle composition comprising:

providing a zein solution stream;

providing an organic solvent fluid stream comprising at least one hydrophobic additive; and providing at least one buffer fluid stream, wherein the zein solution stream, organic solvent fluid stream and buffer fluid stream are separately delivered to a chamber for mixing at one or more rates sufficient to flash precipitate composite nanoparticles including the hydrophobic additive encapsulated by a shell comprising the zein.

* * * * *